(12) United States Patent
Sukumar et al.

(10) Patent No.: US 8,669,105 B2
(45) Date of Patent: Mar. 11, 2014

(54) METHODS FOR ASSAYING RESPONSES TO VACCINES

(75) Inventors: Selva Sukumar, Berkeley, CA (US); Mohey Eldin M. El Shikh, Richmond, VA (US); John G. Tew, Mechanicsville, VA (US); Guzman Sanchez-Schmitz, Orlando, FL (US); Donald Drake, III, Orlando, FL (US); Luis Mosquera, Oviedo, FL (US); Conan Li, Los Altos, CA (US); Anatoly M. Kachurin, Orlando, FL (US); Russell Higbee, Orlando, FL (US); Heather Fahlenkamp, Cleveland, OK (US); Eric Mishkin, Winter Springs, FL (US); William L. Warren, Orlando, FL (US)

(73) Assignees: Sanofi Pasteur Vaxdesign Corp., Orlando, FL (US); Virginia Commonwealth University, Richmond, VA (US)

( * ) Notice: Subject to any disclaimer, the term of this patent is extended or adjusted under 35 U.S.C. 154(b) by 0 days.

(21) Appl. No.: 13/167,131

(22) Filed: Jun. 23, 2011

(65) Prior Publication Data

US 2011/0269176 A1 Nov. 3, 2011

Related U.S. Application Data

(62) Division of application No. 11/642,938, filed on Dec. 21, 2006, now Pat. No. 8,003,387.

(60) Provisional application No. 60/752,034, filed on Dec. 21, 2005.

(51) Int. Cl.
*C12N 5/00* (2006.01)
*C12N 5/02* (2006.01)

(52) U.S. Cl.
USPC ............................ 435/375; 435/382; 435/404

(58) Field of Classification Search
None
See application file for complete search history.

(56) References Cited

U.S. PATENT DOCUMENTS

| | | |
|---|---|---|
| 5,008,116 A | 4/1991 | Cahn |
| 5,160,490 A | 11/1992 | Naughton et al. |
| 5,354,686 A | 10/1994 | Haberman |
| 5,562,910 A | 10/1996 | Daynes et al. |
| 5,725,856 A | 3/1998 | Hudziak et al. |
| 5,739,001 A | 4/1998 | Brown et al. |
| 5,750,329 A | 5/1998 | Quinn et al. |
| 5,785,964 A | 7/1998 | Naughton et al. |
| 6,143,501 A | 11/2000 | Sittinger |
| 6,177,282 B1 | 1/2001 | McIntyre |
| 6,274,378 B1 | 8/2001 | Steinman et al. |
| 6,479,064 B1 | 11/2002 | Atala |
| 6,541,225 B1 | 4/2003 | Li |
| 6,835,550 B1 | 12/2004 | Estell et al. |
| 2002/0155108 A1 | 10/2002 | Barbera-Guillem et al. |
| 2003/0109042 A1 | 6/2003 | Wu et al. |
| 2003/0147923 A1 | 8/2003 | Klaviniskis |
| 2003/0199006 A1 | 10/2003 | Britz et al. |
| 2003/0207287 A1 | 11/2003 | Short |
| 2004/0009943 A1 | 1/2004 | Semple et al. |
| 2004/0109876 A1 | 6/2004 | Yamamoto et al. |
| 2004/0234510 A1 | 11/2004 | Mochitate |
| 2005/0191743 A1 | 9/2005 | Wu et al. |
| 2005/0229264 A1 | 10/2005 | Chang et al. |
| 2005/0282148 A1 | 12/2005 | Warren et al. |
| 2006/0078540 A1 | 4/2006 | Warren et al. |
| 2006/0105454 A1 | 5/2006 | Son et al. |
| 2006/0270029 A1 | 11/2006 | Warren et al. |
| 2006/0275270 A1 | 12/2006 | Warren et al. |
| 2007/0015136 A1 | 1/2007 | Sanchez-Schmitz et al. |
| 2007/0141552 A1 | 6/2007 | Warren et al. |
| 2007/0154956 A1 | 7/2007 | Warren et al. |
| 2007/0178076 A1 | 8/2007 | Drake et al. |
| 2007/0218054 A1 | 9/2007 | Sukumar et al. |
| 2008/0008653 A1 | 1/2008 | Tew et al. |
| 2009/0011455 A1 | 1/2009 | Warren et al. |
| 2009/0104221 A1 | 4/2009 | El Shikh et al. |
| 2009/0117581 A1 | 5/2009 | Warren et al. |

FOREIGN PATENT DOCUMENTS

| | | |
|---|---|---|
| EP | 0358506 | 9/1989 |
| EP | 1013668 | 6/2000 |
| EP | 1437147 | 9/2002 |

(Continued)

OTHER PUBLICATIONS

Feldman et al Transplant. Proc. 1998, 30, 4126-4127.*

(Continued)

*Primary Examiner* — Michail Belyavskyi
(74) *Attorney, Agent, or Firm* — Roylance, Abrams, Berdo & Goodman, L.L.P.

(57) ABSTRACT

The present invention incorporates germinal centers (GCs) into three-dimensional (3D) engineered tissue constructs (ETCs). In an embodiment, we have incorporated the GC in the design of an artificial immune system (AIS) to examine immune responses to vaccines and other compounds. Development of an in vitro GC adds functionality to an AIS, in that it enables generation of an in vitro human humoral response by human B lymphocytes that is accurate and reproducible, without using human subjects. The invention also permits evaluation of, for example, vaccines, allergens, and immunogens, and activation of human B cells specific for a given antigen, which can then be used to generate human antibodies. In an embodiment of the present invention the function of the in vitro GC is enhanced by placing FDCs and other immune cells in a 3D ETC; FDCs appear more effective over a longer time (antibody production is sustained for up to about 14 days.

21 Claims, 16 Drawing Sheets

(56) References Cited

FOREIGN PATENT DOCUMENTS

| | | |
|---|---|---|
| EP | 1970444 | 12/2006 |
| JP | 3-10674 | 1/1991 |
| JP | 8-507860 | 8/1996 |
| WO | 94/20142 | 9/1994 |
| WO | WO 99/12972 | 3/1999 |
| WO | WO 99/15629 | 4/1999 |
| WO | WO 99/43788 | 9/1999 |
| WO | WO 99/49319 | 9/1999 |
| WO | WO 03/041568 | 5/2003 |
| WO | WO 03/050271 | 6/2003 |
| WO | WO 2004/031361 | 4/2004 |
| WO | WO 2004/101773 | 11/2004 |
| WO | WO 2005/013896 | 2/2005 |
| WO | WO 2005/072088 | 8/2005 |
| WO | WO 2005/104755 | 11/2005 |
| WO | WO 2007/075979 | 7/2007 |
| WO | WO 2007/106559 | 9/2007 |
| WO | WO 2007/108835 | 9/2007 |
| WO | WO 2007/146267 | 12/2007 |

OTHER PUBLICATIONS

Cochlovius et al., Modern Drug Discovery, 2003, pp. 33-38.*
Groth et al. "T cell activation: in vivo veritas" Immunology and Cell Biology 2004, 82: 260-2688.*
Ansel, et al., "A Chemokine-Driven Positive Feedback Loop Organizes Lymphoid Follicles", Nature, vol. 406, pp. 309-314 (2000).
Aydar et al. (2005) *J. Immunol.* 174, 5358-5366.
Badylak, S.F. et al., "*Small Intestinal Submucosa: A Substrate for in vitro Cell Growth*," J. Biomater. Sci. Polymer Edn. (1998), vol. 9, No. 8, pp. 863-878.
Bai et al., "*Generation of Dendritic Cells From Human Bone Marrow Mononuclear Cells: Advantages From Clinical Applications in Comparison to Peripheral Blood Monocyte Derived Cells,*" International Journal of Oncology, (2002), 20(2), pp. 247-253.
Banchereau, et al., "Dendritic Cells and the Control of Immunity", Nature, vol. 392, pp. 245-252 (1998).
Banchereau, et al., "Immunobiology of Dendritic Cells", Annu. Rev. Immunol., vol. 18, pp. 767-811 (2000).
Baumgarth, "A Two-Phase Model of B-Cell Activation", Immunological Review, vol. 176, pp. 171-180 (2000).
Benbrook et al., "Organotypic cultures represent tumor microenvironment for drug testing," Drug Discovery Today: Disease Models, 3(2), pp. 143-148 (2005).
Berman, et al., "Roles of Platelet/Endothelial Cell Adhesion Molecule-1 (PECAM-1, CD31) in Natural Killer Cell Transendothelial Migration and Beta 2 Integrin Activation", The Journal of Immunology, vol. 156, pp. 1515-1524 (1996).
Birkness et al., A Tissue Culture Bilayer Model to Study the Passage of Neisseria Meningitidis, *Infection and Immunity*, Feb. 1995, p. 402-409, vol. 63, No. 2.
Birkness et al., An In Vitro Tissue Culture Bilayer Model to Examine Early Events in Mycobacterium Tuberculosis Infection, *Infection and Immunity*, Feb. 1999, p. 653-658, vol. 67, No. 2.
Bogdan, et al., "Fibroblasts as Host Cells in Latent Leishmaniosis", J. Exp. Med., vol. 191, pp. 2121-2129 (2000).
Boni et al. (2006) *Eur. J. Immunol.* 36, 3157-3166.
Brandtzaeg, P. et al., "*Mucosal B Cells: Phenotypic Characteristics, Transcriptional, Regulation, and Homing Properties*," Immunological Reviews (2005), vol. 206, pp. 32-63.
Bromelow, K. V. et al., "*Whole Blood Assay for Assessment of the Mixed Lymphocyte Reaction*," Journal of Immunological Methods, (2001), 247(1-2), pp. 1-8.
Büchele, S. et al., "*Presentation of Tetanus Toxoid to Autologous T Cells by Dendritic Cells Generated From Human Blood. Improved Specificity With Dendritic Cells Generated Without Fetal Calf Serum*," Advances in Experimental Medicine and Biology, (1997), vol. 417, pp. 233-237.
Buchler et al., Generation of antigen-loaded dendritic cells in a serum-free medium using different cytokine combinations. *Vaccine*, 21, 877-882 (2003).
Butcher, et al., "Lymphocyte Trafficking and Regional Immunity", Advances in Immunology, vol. 72, pp. 209-253 (1999).
Castro, et al., "Spleen-Derived Stromal Cells. Adhesion Molecules Expression and Lymphocyte Adhesion to Reticular Cells", Eur. J. Cell. Biol., vol. 74, 321-328 (1997).
Caux et al., Functional CD40 on B Lymphocytes and Dendritic Cells, Res. Immunol. 145:235-239 (1994).
Caux et al. (1995) *J. Immunol.* 155, 5427-5435.
Cayeux et al. (1999) *Eur. J. Immunol.* 29, 225-234.
Chen, et al., "A Film Tension Theory of Phagocytosis", Journal of Colloid and Interface Science, vol. 190, pp. 118-133 (1997).
Chou, et al., "The Detection of the HLA-B27 Antigen by Immunomagnetic Separation and Enzyme-Linked Immunosorbent Assay-Comparison with a Flow Cytometric Procedure", Journal of Immunological Methods, vol. 255, pp. 15-22 (2001).
Clayton et al., Clin. Exp. Immunol., 2003, v.132, p. 174-179.
Crivellato, et al., "Stromal Cell Organisation in the Mouse Lymph Node. A Light and Electron Microscopic Investigation Using the Zinc Iodide-Osmium Technique", J. Anat., vol. 190, pp. 85-92 (1997).
Cyster, "Chemokines and the Homing of Dendritic Cells to the T Cell Areas of Lymphoid Organs", J. Exp. Med. vol. 189, No. 3, pp. 447-450 (1999).
Cyster, et al., "Follicular Stromal Cells and Lymphocyte Homing to Follicles", Immunological Reviews, vol. 176, pp. 181-193 (2000).
D'Amico et al., Adhesion, transendothelial migration, and reverse transmigration of in vitro cultured dendritic cells. *Blood* 92:207-214 (1998).
Danke, et al., "HLA Class II-Restricted CD4+ T Cell Responses Directed Against Influenza Viral Antigens Postinfluenza Vaccination", The Journal of Immunology, vol. 171, pp. 3163-3169 (2003).
Denkbas, et al., "Magnetic Chotosan Microspheres: Preparation and Characterization", Reactive & Functional Polymers, vol. 50, pp. 225-232 (2002).
Dubey et al. (2005) *J. Clin. Endocrin & Met.*, 90, 247-255.
Dubois, et al., "Dendritic Cells Enhance Growth and Differentiation of CD40-Activated B Lymphocytes", J. Exp. Med., vol. 185, pp. 941-951 (1997).
Dubois et al., J. Leukocyte Biology, 1999, v.66, p. 224-230.
Edelman et al, A Cultureal Renaissance: In Vitro Cell Biology Embraces Three-Dimensional Context. Exp Neurol. 2005, vol. 192, pp. 1-6.
El Shikh, M. et al., "*Follicular Dendritic Cells Stimulated by Collagen Type I Develop Dendrites and Networks In Vitro*," Cell and Tissue Research, (2007), 329(1), pp. 81-89.
Forster, et al., "CCR7 Coordinates the Primary Immune Response by Establishing Functional Microenvironments in Secondary Lymphoid Organs", Cell., vol. 99, pp. 23-33 (1999).
Fransson, et al., "Culture of Human Epidermal Langerhans Cells in a Skin Equivalent", British Journal of Dermatology, vol. 139, pp. 598-604 (1998).
Friedl, et al., "CD4+ T Lymphocytes Migrating in Three-Dimensional Collagen Lattices Lack Focal Adhesions and Utilize Beta 1 Integrin-Independent Strategies for Polarization, Interaction with Collagen Fibers and Locomotion", Eur. J. Immunol., vol. 28, pp. 2331-2343 (1998).
Fulcher, et al., "B-Cell Activation Versus Tolerance—The Central Role of Immunoglobulin Receptor Engagement and T-Cell Help", Int. Rev. Immunol., vol. 15, pp. 33-52 (1997).
Furie, et al., "Migration of Neutrophils Across Endothelial Monolayers is Stimulated by Treatment of the Monolayers with Interleukin-1 or Tumor Necrosis Factor-Alpha", The Journal of Immunology, vol. 143, pp. 3309-3317 (1989).
Furuyama, A. et al., "*Assembly of Basement Membrane in vitro by Cooperation Between Alveolar Epithelial Cells and Pulmonary Fibroblasts*," Cell Structure and Function (1997), vol. 22, pp. 603-614.
Galibert, et al., "CD40 and B Cell Antigen Receptor Dual Triggering of Resting B Lymphocytes Turns on a Partial Germinal Center Phenotype", J. Exp. Med., vol. 183, pp. 77-85 (1996).

(56) References Cited

OTHER PUBLICATIONS

Gansuvd et al., Human Immunol., 2003, v.64, p. 427-439.
Garside, et al., "Visualization of Specific B and T Lumphocyte Interactions in the Lymph Node", Science, vol. 281, pp. 96-99 (1998).
Gergel, et al., "Activation of Endothelium by *Borrelia burgdorferi* In Vitro Enhances Transmigration of Specific Subsets of T Lymphocytes", Infection and Immunity, vol. 69, pp. 2190-2197 (2001).
Gretz, et al., "Cords, Channels, Corridors and Conduits: Critical Architectural Elements Facilitating Cell Interactions in the Lymph Node Cortex", Immunological Reviews, vol. 156, pp. 11-24 (1997).
Gretz, et al., "Lymph-borne Chemokines and Other Low Molecular Weight Molecules Reach High Endothelial Venules Via Specialized Conduits While a Functional Barrier Limits Access to the Lymphocyte Microenvironments in Lymph Node Cortex", The Journal of Experimental Medicine, vol. 192, pp. 1425-1439 (2000).
Gretz, et al., "Sophisticated Strategies for Information Encounter in the Lymph Node: The Reticular Network as a Conduit of Soluble Information and a Highway for Cell Traffic", The Journal of Immunology, vol. 157, pp. 495-499 (1996).
Grouard et al., Regulation of Human B Cell activation by Follicular Dendritic Cell and T Cell Signals. Current Topics Microbiol. Immunol. 201:105-117 (1995).
Gundersen, et al., "Magnetic Bead Antigen Capture Enzyme-Linked Immunoassay in Microtitre Trays for Rapid Detection of Schistosomal Circulating Anodic Antigen", Journal of Immunological Methods, vol. 148, pp. 1-8 (1992).
Gunn, et al., "Mice Lacking Expression of Secondary Lymphoid Organ Chemokine Have Defects in Lymphocyte Homing and Dentritic Cell Localization", J. Exp. Med., vol. 189, pp. 451-460 (1999).
Gunzer, et al., "Antigen Presentation in Extracellular Matrix: Interactions of T Cells with Dendritic Cells are Dynamic, Short Lived, and Sequential", Immunity, vol. 13, pp. 323-332 (2000).
Hasbold, et al., "Quantitative Analysis of Lymphocyte Differentiation and Proliferation in Vitro Using CarboxyFluorescein Diacetate Succinimidyl Ester", Immunology and Cell Biology, vol. 77, pp. 516-522 (1999).
Hashimoto, K., et al., Direct Observation and Analysis of Spatiotemporal Dynamics of Individual Living Monocyte During Transendothelial Migration. Atherosclerosis 177(1):19-27 (Nov. 2004).
Hashimoto, K., et al., Direct Observation and Analysis of Spatiotemporal Dynamics of Individual Living Monocyte During Transendothelial Migration. Collection of Papers from 16th Bioengineering Conference, Jan. 21, 2004, pp. 13-14.
Higbee, R., et al., An Immunologic Model for Rapid Vaccine Assessment—A Clinical Trial in a Test Tube. ALTA 37, Suppl. 1, 19-27 (2009).
Inaba et al., Clustering of Dendritic Cells, Helper T Lymphocytes, and Histocompatible B Cells During Primary Antibody Response In vitro, J. Exp. Med. 160:858-876 (1984).
Irvine, et al., "Nanoscale Clustering of RGD Peptides at Surfaces Using Comb Polymers. 1. Synthesis and Characterization of Comb Thin Films", Biomacromolecules, vol. 2, pp. 85-94 (2001).
Jenkins, et al., "In Vivo Activation of Antigen-Specific CD4 T Cells", Annu. Rev. Immunol., vol. 19, pp. 23-45 (2001).
Junt, et al., "Antiviral Immune Responses in the Absence of Organized Lymphoid T Cell Zones in *plt/plt* Mice", The Journal of Immunology, vol. 168, pp. 6032-6040 (2002).
Kabashima, et al., "Prostaglandin $E_2$-EP4 Signaling Initiates Skin Immune Responses by Promoting Migration and Maturation of Langerhans Cells", Nature Medicine, vol. 9, pp. 744-749 (2003).
Kadowaki, et al., "Subsets of Human Dendritic Cell Precursors Express Different Toll-Like Receptors and Respond to Different Microbial Antigens", J. Exp. Med. vol. 194, No. 6, pp. 863-869 (2001).
Kaldjian, et al., "Spatial and Molecular Organization of Lymph Node T Cell Cortex: A Labyrinthine Cavity Bounded by an Epithelium-Like Monolayer of Fibroblastic Reticular Cells Anchored to Basement Membrane-like Extracellular Matrix", International Immunology, vol. 13, pp. 1243-1253 (2001).
Katakai et al., Lymph Node Fibroblastic Reticular Cells Construct the Stromal Reticulum via Contact with Lymphocytes, J. Exp. Med. 200(6):783-795 (2004).
Khademhosseini et al., "*Microscale Technologies for Tissue Engineering and Biology*," Proc. Natl. Acad. Sci. USA, vol. 103, pp. 2480-2487 (2006).
Kim et al., "*Three-Dimensional Tissue Culture Models in Cancer Biology*," Seminars in Cancer Biology, (2005), 15(5), pp. 365-377.
Kim, H.-J. et al, Establishment of Early Lymphoid Organ Infrastructure in Transplanted Tumors Mediated by Local Production of Lymphotoxin α and in Combined Absence of Functional B and T Cells. In J. of Immunology, vol. 172:4037-4047 (2004).
Kosco, M. H. et al., "*Folicular Dendritic Cell-Dependent B-Cell Proliferation and In Vitro Germinal Center*," Lymphatic Tissues In Vivo Immune Responses, (1991), pp. 687-690.
Kosco, M. H. et al., "*Follicular Dendritic Cell-Dependent Adhesion and Proliferation of B Cells In Vitro*," Journal of Immunology, (1992), 148(8), pp. 2331-2339.
Kosco, M. H. et al., "*Follicular Dendritic Cells and Germinal Center Formation In-Vitro*," Accessory Cells in HIV and Other Retroviral Infections: Morphological and Functional Aspects; Workshop on Morphological and Functional Aspects of Accessory Cells in retroviral Infections, Hamberg, Germany, 23-24, p. 44-49 (1991).
Kosco-Vilbois, "Are Follicular Dendritic Cells Really Good for Nothing", Nature Reviews Immunology, vol. 3, pp. 764-769 (2003).
Kourilov, et al., "Magnetic-Bead Enzyme-Linked Immunosorbent Assay Verifies Adsorption of Ligand and Epitope Accessibility", Analytical Biochemistry, vol. 311, pp. 166-170 (2002).
Larsson, et al., "Requirement of Mature Dendritic Cells for Efficient Activation of Influenza A-Specific Memory CD8 + T Cells", The Journal of Immunology, vol. 165, pp. 1182-1190 (2000).
LeBedis, et al., "Peripheral Lymph Node Stromal Cells Can Promote Growth and Tumorigenicity of Breast Carcinoma Cells Through the Release of IGF-I and EGF", Int. J. Cancer, vol. 100, pp. 2-8 (2002).
Levenberg, S. et al., "*Advances in Tissue Engineering*," Current Topics in Developmental Biology, (2004), vol. 61, pp. 113-134.
Luk, et al., "Rapid and Sensitive Detection of *Salmonella* (O:6,7) by Immunomagnetic Monoclonal Antibody-Based Assays", Journal of Immunological Methods, vol. 137, pp. 1-8 (1991).
Lukas, et al., "Human Cutaneous Dendritic Cells Migrate Through Dermal Lymphatic Vessels in a Skin Organ Culture Model", The Journal of Investigative Dermatology, vol. 106, pp. 1293-1299 (1996).
Manna, P. et al., "Differentiation and Functional Maturation of Human CD14<+> Adherent Peripheral Blood Monocytes by Xenogeneic Endothelial Cells: Up-Regulation of Costimulation Cytokine Generation, and Toll-Like Receptors," Transplantation, (2002), 74(2), pp. 243-252.
Matsumoto, et al., "Affinity Maturation Without Germinal Centres in Lymphotoxin-α-Deficient Mice", Nature, vol. 382, pp. 462-466 (1996).
Mebius, "Organogenesis of Lymphoid Tissues", Nat. Rev. Immunol, vol. 3, pp. 292-303 (2003).
Mellman, et al., "Dendritic Cells: Specialized and Regulated Antigen Processing Machines", Cell, vol. 106, pp. 255-258 (2001).
Miller, et al., "Two-Photon Imaging of Lymphocyte Motility and Antigen Response in Intact Lymph Node", Science, vol. 296, pp. 1869-1873 (2002).
Mori, et al., "Mice Lacking Expression of the Chemokines CCL21-ser and CCL19 (plt Mice) Demonstrate Delayed but Enhanced T Cell Immune Responses", J. Exp. Med., vol. 193, No. 2, pp. 207-217 (2001).
Moser et al. (2000) *Nature Immunol.* 1, 199-205.
Nakamura, M. et al., "*Expression of Leptin in Two-layered Culture of Gastric Mucous Cells and Fibroblasts: Effect of Helicobacter pylori Attachment*," Aliment Pharmacol Ther. (2004), vol. 20, suppl. 1, pp. 125-130.
Nakatsu, M. N. et al., "*Angiogenic Sprouting and Capillary Lumen Formation Modeled by Human Umbilical Vein Endothelial Cells (HUVEC) in Fibrin Gels: The Role of Fibroblasts and Angiopoietin-1*," Microvascular Research (2003), vol. 66, pp. 102-112.

(56) References Cited

OTHER PUBLICATIONS

Neves, A. R. et al., "*Dendritic Cells Derived From Metastatic Cancer Vaccinated With Allogeneic Dendritic Cell-Autologous Tumor Cell Hybrids Express More CD86 and Induce Higher Levels of Interferon-Gamma in Mixed Lymphocyte Reactions*," Cancer Immunology and Immunotherapy, (2005), 54(1), pp. 61-66.
Oehler et al. (2000) *Ann. Hematol.*, 79, 355-362.
Okamoto et al, Artificial Lymph Nodes Induce Potent Secondary Immune Response in Naïve and Immunodeficient Mice. J. Clin. Invest. Apr. 2007, vol. 117, No. 4, pp. 997-1007.
Parker, "T Cell-Dependent B Cell Activation", Annu. Rev. Immunol., vol. 11, pp. 331-360 (1993).
Pasparakis, et al., "Immune and Inflammatory Responses in TNFα Deficient Mice: A Critical Requirement for TNFα in the Formation of Primary B Cell Follicles, Follicular Dendritic Cell Networks and Germinal Centers, and in the Maturation of the Humoral Immune Response", J. Exp. Med., vol. 184, pp. 1397-1411 (1996).
Phillips, et al., "Activation of Pertussis Toxin-Sensitive CXCL12 (SDF-1) Receptors Mediates Transendothelial Migration of T Lymphocytes Across Lymph Node High Endothelial Cells", Eur. J. Immunol., vol. 32, pp. 837-847 (2002).
Podgrabinska, et al., "Molecular Characterization of Lymphatic Endothelial Cells", Proc. Natl. Acad. Sci. U.S.A., vol. 99, No. 25, pp. 16069-16074 (2002).
Portner, R et al, Chapter 2: An Overview on Bioreactor Design, Prototyping, and Process Control for Reproducible Three-Dimensional Tissue Culture. In Drug Testing In Vitro: Breakthrough Cell Cultur Technology. Eds. U. Marx and V. Sandig 2006: Wiley-VCH, pp. 65-69.
Poznansky, et al., "Efficient Generation of Human T Cells From a Tissue-Engineered Thymic Organoid", Nature Biotechnology, vol. 18, pp. 729-734 (2000).
Qu, et al., "Autocrine Type I IFN and Contact with Endothelium Promote the Presentation of Influenza A Virus by Monocyte-Derived APC", The Journal of Immunology, vol. 170, pp. 1010-1018 (2003).
Randolph, et al., "A Physiologic Function for p-Glycoprotein (MDR-1) During the Migration of Dendritic Cells from Skin Via Afferent Lymphatic Vessels", Proc. Natl. Acad. Sci., vol. 95, pp. 6924-2929 (1998).
Randolph, et al., "A Soluble Gradient of Endogenous Monocyte Chemoattractant Protein-1 Promotes the Transendothelial Migration of Monocytes In Vitro", The Journal of Immunology, vol. 155, pp. 3610-3618 (1995).
Randolph, et al., "Differentiation of Monocytes into Dendritic Cells in a Model of Transendothelial Trafficking", Science, vol. 282, pp. 480-483 (1998).
Randolph, et al., "Mononuclear Phagocytes Egress from an In Vitro Model of the Vascular Wall by Migrating Across Endothelium in the Basal to Apical Direction: Role of Intercellular Adhesion Molecule 1 and the CD11/CD18 Integrins", J. Exp. Med., vol. 183, pp. 451-462 (1996).
Randolph, et al., "Role of Tissue Factor in Adhesion of Mononuclear Phagocytes to and Trafficking Through Endothelium in Vitro", Blood, vol. 92, pp. 4167-4177 (1998).
Randolph, et al., "The CD16(+) (FcγRIII(+)) Subset of Human Monocytes Preferentially Becomes Migratory Dendritic Cells in a Model Tissue Setting", J. Exp. Med., vol. 196, No. 4, pp. 517-527 (2002).
Razanajaona, et al., In Vitro Triggering of Somatic Mutation in Human Naïve B Cells', The Journal of Immunology, vol. 159, pp. 3347-3353 (1997).
Regnier, et al., "Integration of Langerhans Cells into a Pigmented Reconstructed Human Epidermis", The Journal of Investigative Dermatology, vol. 109, No. 4, pp. 510-512 (1997).
Robbiani, et al., "The Leukotriene C4 Transporter MRP1 Regulates CCL19 (MIP-3β, ELC)-Dependent Mobilization of Dendritic Cells to Lymph Nodes", Cell, vol. 103, pp. 757-768 (2000).
Roos et al. (2005) *Expert Opin. Drug Metab. Toxicol.* 1, 187-202.

Rot, "In Situ Binding Assay for Studying Chemokine Interactions with Endothelial Cells", Journal of Immunological Methods, vol. 273, pp. 63-71 (2003).
Ruco, et al., "Expression and Cell Distribution of the Intercellular Adhesion Molecule, Vascular Cell Adhesion Molecule, Endothelial Leukocyte Adhesion Molecule, and Endothelial Cell Adhesion Molecule (CD31) in Reactive Human Lymph Nodes and in Hodgkin's Disease", American Journal of Pathology, vol. 140, pp. 1337-1344 (1992).
Safarik, et al., "Use of Magnetic Techniques for the Isolation of Cells", Journal of Chromatography B, vol. 722, pp. 33-53 (1999).
Santini et al. (2000) *J. Exp. Med.* 191, 1777-1788.
Sarradell et al. (2003) *Vet. Pathol.*, 40, 395-404.
Seguin, R. et al., "*Human Brain Endothelial Cells Supply Support for Monocyte Immunoregulartory Functions*," Journal of Neuroimmunology, (2003), 135(1-2), pp. 96-106.
Sieben, et al., "Comparison of Different Particles and Methods for Magnetic Isolation of Circulating Tumor Cells", Journal of Magnetism and Magnetic Materials, vol. 225, pp. 175-179 (2001).
Simmingskoeld et al., Mononuclear leucocyte chemotaxis in Boyden chambers: inhibition by subantimitotic concentrations of antitubulins. *Scand. J. Immunol.* 7:233-238 (1978).
Skibinski, et al., "Enhancement of Terminal B Lymphocyte Differentiation in Vitro by Fibroblast-Like Stromal Cells from Human Spleen", Eur. J. Immunol., vol. 28, pp. 3940-3948 (1998).
Skibinski, et al., "The Role of Hepatocyte Growth Factor and Its Receptor c-met in Interactions Between Lymphocytes and Stromal Cells in Secondary Human Lymphoid Organs", Immunology, vol. 102, pp. 506-514 (2001).
Soderberg, O. et al., "*The Human Follicular Dendritic Cell Line FDC-1 Binds Immune Complexes and Promotes Somatic Hypermutation*," Blood, (2001), 98(11 part 2), pp. 40b.
Sprent, et al., "Antigen-Induced Selective Recruitment of Circulating Lymphocytes", Cellular Immunology, vol. 2, pp. 171-181 (1971).
Stoll, et al., "Dynamic Imaging of T Cell-Dendritic Cell Interactions in Lymph Nodes", Science, vol. 296, pp. 1873-1876 (2002).
Stuart, et al., "The Human Reticular Cell: Morphology and Cytochemistry", J. Pathol, vol. 103, pp. 41-47 (1971).
Suematsu, et al., "Generation of a Synthetic Lymphoid Tissue-Like Organoid in Mice", Nature Biotechnology, vol. 22, No. 12, pp. 1539-1545 (Dec. 2004).
Takeuchi et al., CCL21 Chemokine Regulates Chemokine Receptor CCR7 Bearing Malignant Melanoma Cells, Clin. Cancer Res. 10:2351-2358 (2004).
Tan et al. (2005) *J. Leuk. Biol.* 78, 319-324.
Tarte et al., Leukemia, vol. 14, 2000, abstract p. 2182.
Tew et al. (2001) *Trends Immunol.* 22, 361-367.
Tew, J. G. et al., "*Follicular Dendritic Cells As Accessory Cells*," Immunological Reviews, (1990), No. 117, pp. 185-211.
Tew, J.G. et al., "*Follicular Dendritic Cells and Presentation of Antigen and Costimulatory Signals to B Cells*," Immunological Reviews (1997), vol. 156, pp. 39-52.
Thompson, H.G. et al., "*A Three-dimensional in vitro Model of Angiogenesis in the Airway Mucosa*," Pulmonary Pharmacology & Therapeutics (2007), vol. 20, pp. 141-148.
Toyama, et al., "Memory B Cells Without Somatic Hypermutation are Generated from Bcl 6 Deficient B Cells", Immunity, vol. 17, pp. 329-339 (2002).
Tsunoda, R. et al., "*Follicular Dendritic Cells In Vitro Modulate the Expression of Fas and Bcl-2 on Germinal Center B Cells*," Cell and Tissue Research, (2000), 299(3), pp. 395-402.
Tsunoda, R. et al., "*Human Follicular Dendritic Cells In Vitro and Follicular Dendritic-Cell-Like Cells*," Cell and Tissue Research, (1997), 288(2), pp. 381-389.
Van Den Berg, et al., "Localization of β 1 Integrins and Their Extracellular Ligands in Human Lymphoid Tissues", American Journal of Pathology, vol. 143, pp. 1098-1110 (1993).
Warren, W., The Front-End of Vaccine Manufacturing: Getting Good Candidates from the Get-Go. Workshop on Science and Technology in North American Rapid Vaccine Manufacturing, Jan. 26, 2007.
Weppler et al., Modulation of Endotoxin-Induced Neutrophil Transendothelial Migration by Alveolar Epithelium in a Defined Bilayer Model, *Experimental Lung Research* 32:10, 455-482 (2006).

(56) References Cited

OTHER PUBLICATIONS

West, et al., "Polymeric Biomaterials with Degradation Sites for Proteases Involved in Cell Migration", Macromolecules, vol. 32, pp. 241-244 (1999).

Wu et al. (2008) *J. Immunol.* 180, 281-290.

Wu, Y. et al., "*Influence of Follicular Dendritic Cells and Primed T Cells on Somatic Hypermutation In In Vitro Germinal Centers*," Journal of Immunology, (2006), 176(suppl. S), pp. S235-S236.

Zhang, S. et al., "*Growth Factors Secreted by Bronchial Epithelial Cells Control Myofibroblast Proliferation: An in vitro Co-culture Model of Airway Remodeling in Asthma*," Laboratory Investigation (1999), vol. 79, No. 4, pp. 395-405.

International Search Report—PCT/US2007/083795, dated May 28, 2008.

International Search Report—PCT/US2008/056720, dated Jul. 29, 2008.

International Search Report—PCT/US08/70107, dated Mar. 13, 2009.

International Search Report—PCT/US06/048959, dated Jan. 13, 2009.

International Search Report—PCT/US07/014826, dated Dec. 30, 2008.

International Search Report—PCT/US08/69172, dated Mar. 25, 2009.

International Search Report—PCT/US07/013745, dated Apr. 18, 2009.

International Search Report—PCT/US05/14444, dated Mar. 21, 2008.

International Search Report—PCT/US06/43563, dated Nov. 29, 2007.

International Search Report—PCT/US06/43712, dated Aug. 8, 2007.

International Search Report—PCT/US07/006532, dated Feb. 18, 2008.

International Search Report—PCT/US07/006571, dated Sep. 21, 2007.

International Search Report—PCT/US07/013871, dated Mar. 3, 2008.

International Search Report—PCT/US06/049128, dated Jun. 12, 2007.

Dynal (Norway): http://www.invitrogen.com/, dated Feb. 17, 2006.

Agowa GMBH (Germany): http://agowade/contentsframes/magneticseparation/particle.html, dated Feb. 17, 2006.

http://www.xcyte.com, dated Feb. 17, 2006.

Protocol for anti-CD3 Activation of T-Cells from E-Bioscience (San Diego, CA): http://www.ebioscience..com/ebioscience/appls/AC145.htm, dated Feb. 17, 2006.

Transwell® Permeable Supports Selection and Use Guide, Corning Corp., pp. 1-12 (2009).

Price, N. et al., Genome-scale microbial in silico models: the constraints-based approach, TRENDS Biotechnol., 2003, vol. 21, No. 4, pp. 162-169.

Nagashima, U. et al., The cutting edge of molecular simulation What can molecular simulation tell us? From micro to macro—From the nature of the molecule to the nature of assembly, Chemical Engineering, 2003, vol. 67, No. 8, pp. 432-435.

Tomita, M. et al., Computer Simulation of Cells, CICSJ Bull., 2001, vol. 19, No. 6, pp. 2-6.

Sun, W.D. et al., An artificial immune system architecture and its applications, IECE Trans. Fundamentals, 2003, vol. E86-A, No. 7, pp. 1858-1868.

Guidry, A.J. et al., A bovine mammary endothelial/epithelial cell culture model of the blood/milk barrier, Can. J. Vet. Res., 1998, vol. 62, pp. 117-121.

Hauser, A. et al., Chemotactic responsiveness toward ligands for CXCR3 and CXCR4 is regulated on plasma blasts during the time course of a memory immune response, J. Immunol., 2002, vol. 169, pp. 1277-1282.

Alt, C. et al., Functional expression of the lymphoid chemokines CCL19 (ELC) and CCL21 (SLC) at the blood-brain barrier suggests their involvement in G-protein-dependent lymphocyte recruitment into the central nervous system during experimental autoimmune encephalomyelitis, Eur. J. Immunol., 2002, vol. 32, pp. 2133-2144.

Ferrero et al. CD14+ CD34+ Peripheral Blood Mononuclear Cells Migrate Across Endothelium and Give Rise to Immunostimulatory Dendritic Cells. J. Immunol. 160:2675-2683 (1998).

\* cited by examiner

Figure 4A
HUVEC *monolayer*
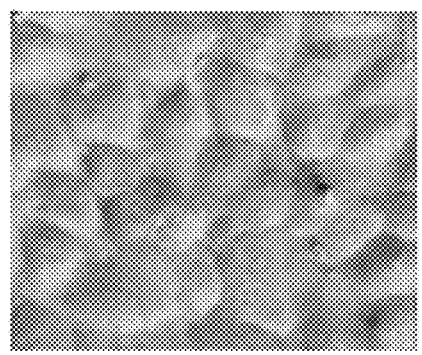 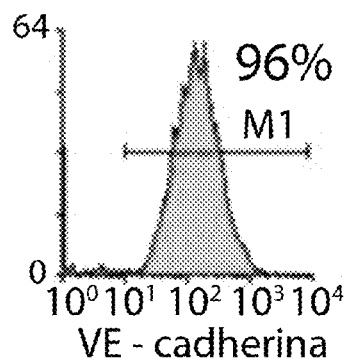
VE - cadherina
Tissue Setting Model
Confluent monlolayer of primary HUVEC cells over a type I bovine collagen matrix
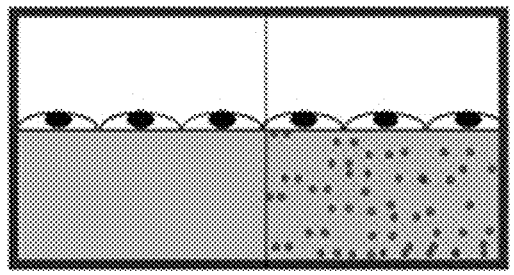
( not stimuli)   ( • stimuli)
*(Randolph GJ et al. Science 1998, 282: 480-483)*

% mature DCs
(HLA-DR +++ / CD83+)

| Stimuli: | R/Ts | S/Es |
|---|---|---|
| Nothing | 7 ± 7 | 0.2 ± 0.4 |
| IL-1 | 15 ± 7 | 0.1 ± 0.5 |
| LPS | 14 ± 2 | 2 ± 2 |
| Zymosan | 47 ± 13 | 2 ± 3 |

LPS = lipopolysaccaride; zymosan = yeast membranes;
IL-1 = interleukine one (Randolph GJ et al. Science 1998, 282: 480-483)

Figure 10

```
Vh186-wt   1 GGTGTCCACT CCCAGGTCCA ACTGCAGCAG CCTGGGGCTG AGCTTGTGAA GCCTGGGGCT
VH186-2    1 .......... .......... GT........ T...A.T.. A..G..A.G .......A..
VH186-8    1 .......... .......... GT........ T...A.T.. A..G..A.G .......A..
VH186-15   1 .......... .......... GT........ T...A.T.. A..G..A.G .......A..
VH186-1    1 .......... ......T.. G........ T...A.... ....GA.... .........C
VH186-22   1 .......... .......... GT........ T...A.T.. A..G..A.G .......A..
VH186-6    1 .......... .......... .......... .......... ....G....G ..........
VH186-24   1 .......... .......... ...A...... ......A... A..G....G ..........

Vh186-wt  61 TCAGTGAAGC TGTCCTGCAA GGCTTCTGGC TACACCTTCA CCAGCTACTG GATGCACTGG
VH186-2   61 .........A A........ .......... .......... .T.A...... .C.AGGT...
VH186-8   61 .........A A........ .......... .......... .T.A...... .C.AGGT...
VH186-15  61 ....C....A A........ .......... .......... .T.A...... .C.AGGT...
VH186-1   61 .........A A........ ....A..... ......A... GT........ ...AG.G...
VH186-22  61 .........A A........ .......... .......... .T.A...... .C.AGGT...
VH186-6   61 .......... .......... .......... .......... .......... ....A.....
VH186-24  61 .......... .......... .......... ....GT.... ...C...... ....A.....

Vh186-wt 121 GTGAAGTAGA GGCCTGGACG AGGCTTGAG TGGATTGGAA GGATTGATCC TAATAGTGGT
VH186-2  121 ..A....... .........A T..A...... .........G AT...T.C.. .GGAG.....
VH186-8  121 ..A....... .........A T..A...... .........G AT...T.C.. .GGAG.....
VH186-15 121 ..A....... .........A T..A...T... .........G AT...T.C.. .GGAG.....
VH186-1  121 ..A....... .........A T......... .........G A....TTA.. .GA.......
VH186-22 121 ..A....... .........A T..A...... .........G AT...T.C.. .GGA......
VH186-6  121 .......... .........A .......... .A........ .T. T...... .TCAGACA..
VH186-24 121 .......... .........A .......... .A........ .T........ .TCAGACAC.

Vh186-wt 181 GGTACTAAGT ACAATGAGAA GTTCAAGAGC AAGGCCACAC TGACTGTAGA CAAACCCTCC
VH186-2  181 TA......C. .......... .......G.. .......... ......C... ..C.T.....
VH186-8  181 TA......C. .......... .......G.. .......... ......C... ..C.T.....
VH186-15 181 TA......C. .......... .......GA. .......... .T......... ....T.....
VH186-1  181 A.......C. .......... .......G.. .......... .T .C...C... T.C.T.....
VH186-22 181 A.......C. .......... .......G.. .......... .T .C...C... T.C.T.....
VH186-6  181 .AA.G.C.C. .....C.AGT .......GA. .......... .T.......... ....T.....
VH186-24 181 .AA...C.C. ...G.C.ATT .......GA. .......... .T.......T.. ....T..C..
```

The number of unique mutations per 10 nucleotide bases are plotted against the base positions.

METHODS FOR ASSAYING RESPONSES TO VACCINES

CROSS REFERENCE TO RELATED CASES

This application is a divisional of U.S. application Ser. No. 11/642,938, filed Dec. 21, 2006, now U.S. Pat. No. 8,003,387, issuing on Aug. 23, 2011, which claims the benefit of U.S. Provisional Application Ser. No. 60/752,034, filed Dec. 21, 2005, both of which are herein incorporated by reference in their entireties.

STATEMENT REGARDING FEDERALLY SPONSORED RESEARCH

This invention was made with government support under contract number NBCHC060058, awarded by the Defense Advanced Research Projects Agency, issued by the U.S. Army Medical Research Acquisition Activity, and administered by the U.S. Department of the Interior-National Business Center. The government has certain rights in the invention.

BACKGROUND OF THE INVENTION

We have previously developed functional in vitro germinal centers (GCs) using naïve murine B cells. The model was studied in two dimensions (2-D) in culture plates. In these murine in vitro GCs, immunoglobulin (Ig) class switching, somatic hypermutation, selection of the high affinity B cells, and affinity maturation were demonstrated. These activities are important to the goal of studying vaccines in vitro. In the in vitro GC, follicular dendritic cells (FDCs) serve two main functions: to facilitate T cell-B cell interaction and to potentiate B cell viability. Both of these functions enable and facilitate activation of specific B cells, antibody production, and differentiation into plasma cells.

In 1968, Szakal and Hanna (*J. Immunol.* 101, 949-962; *Exp. Mol. Pathol.* 8, 75-89) and Nossal et al. (*J. Exp. Med.* 127, 277-290) published the first descriptions and electron micrographs of what are now known as follicular dendritic cells (FDCs). Both groups used $^{125}$I-labeled antigens and examined autoradiographs of the follicles in rodent spleens or lymph nodes using electron microscopy. Both groups found that radiolabel persisted on or near the surface of highly convoluted fine cell processes of dendritic-type cells with peculiar, irregularly shaped, euchromatic nuclei. The fine cell processes formed an elaborate meshwork around passing lymphocytes, allowing extensive cell-cell contact. Several names have been used for these cells but a nomenclature committee recommended the name "follicular dendritic cell" and the abbreviation "FDC" and these have been generally adopted (Tew et al. (1982) *J. Reticuloendothelial Soc.* 31, 371-380).

The ability of FDCs to trap and retain antigen-antibody complexes, together with their follicular location, distinguishes them from other cells, including other dendritic cells (DCs). FDCs bearing specific antigens are required for full development of GCs (Kosco et al. (1992) *J. Immunol.* 148, 2331-2339; Tew et al. (1990) *Immunol. Rev.* 117, 185-211) and are believed to be involved in Ig class switching, production of B memory cells, selection of somatically mutated B cells with high affinity receptors, affinity maturation, induction of secondary antibody responses, and regulation of serum IgG with high affinity antibodies (Tew et al. (1990) *Immunol. Rev.* 117, 185-211; Berek & Ziegner (1993) *Immunol. Today* 14, 400-404; MacLennan & Gray (1986) *Immunol. Rev.* 91, 61-85; Kraal et al. (1982) *Nature* 298, 377-379; Liu et al. (1996) *Immunity* 4, 241-250; Tsiagbe et al. (1992) *Immunol. Rev.* 126, 113-141). Many researchers have worked with FDCs in culture in 2D with the general idea of mimicking an in vivo GC. An appreciation of the accessory functions of FDCs and regulation of these functions is important to an understanding of fully functional and mature antibody responses.

FDC development is B cell-dependent; FDCs are not detectable in, for example, SCID mice, mice treated with anti-mu (to remove B cells), or mice lacking the mu chain (where B cells do not develop) (MacLennan & Gray (1986) *Immunol. Rev.* 91, 61-85; Kapasi et al. (1993) *J. Immunol.* 150, 2648-2658). In T cell-deficient mice (e.g., nude mice), FDCs do develop, although the development is retarded and the FDCs do not appear to express many FDC markers (Tew et al. (1979) *Aust. J. Exp. Biol. Med. Sci.* 57, 401-414).

Reconstitution of FDCs in SCID mice occurs best when both B cells and T cells are adoptively transplanted, suggesting that T cells are also involved in FDC development (Kapasi et al. (1993) *J. Immunol.* 150, 2648-2658). Disruption of LT/TNF or the cognate receptors disrupts lymph node organogenesis and interferes with the development of FDC networks (De Togni et al. (1994) *Science* 264, 703-707; Rennert et al. (1996) *J. Exp. Med.* 184, 1999-2006; Chaplin & Fu (1998) *Curr. Opin. Immunol.* 10, 289-297; Endres et al. (1999) *J. Exp. Med.* 189, 159-168; Ansel et al. (2000) *Nature* 406, 309-314). As summarized by Debard et al. (1999), it is known that a lack of LTα, LTβ, TNFαR1, and LTβR interferes with the development of FDC networks (*Semin. Immunol.* 11, 183-191). B cells are an important source of LTα/β heterotrimers, consistent with data indicating that FDC development is B cell-dependent (Endres et al. (1999) *J. Exp. Med.* 189, 159-168; Ansel et al. (2000) *Nature* 406, 309-314; Fu et al. (1998) *J. Exp. Med.* 187, 1009-1018).

The functional element of a mammalian lymph node is the follicle, which develops a GC when stimulated by an antigen. The GC is an active area in a lymph node, where important interactions occur in the development of an effective humoral immune response. Upon antigen stimulation, follicles are replicated and an active human lymph node may have dozens of active follicles, with functioning GCs. Interactions between B cells, T cells, and FDCs take place in GCs. Various studies of GCs in vivo indicate that the following events occur there:

- immunoglobulin (Ig) class switching,
- rapid B cell proliferation (GC dark zone),
- production of B memory cells,
- accumulation of select populations of antigen specific T cells and B cells,
- hypermutation,
- selection of somatically mutated B cells with high affinity receptors,
- apoptosis of low affinity B cells,
- affinity maturation,
- induction of secondary antibody responses, and
- regulation of serum immunoglobulin G (IgG) with high affinity antibodies.

Similarly, data from in vitro GC models indicate that FDCs are involved in:

- stimulating B cell proliferation with mitogens and it can also be demonstrated with antigen (Ag),
- promoting production of antibodies including recall antibody responses,
- producing chemokines that attract B cells and certain populations of T cells, and
- blocking apoptosis of B cells.

While T cells are necessary for B cell responses to T cell-dependent antigens, they are not sufficient for the development of fully functional and mature antibody responses that are required with most vaccines. FDCs provide important assistance needed for the B cells to achieve their full potential (Tew et al. (2001) Trends Immunol. 22, 361-367).

Humoral responses in vaccine assessment can be examined using an artificial immune system (AIS). Accessory functions of follicular dendritic cells and regulation of these functions are important to an understanding of fully functional and mature antibody responses.

Important molecules have been characterized by blocking ligands and receptors on FDCs or B cells. FDCs trap antigen-antibody complexes and provide intact antigen for interaction with B cell receptors (BCRs) on GC B cells; this antigen-BCR interaction provides a positive signal for B cell activation and differentiation. Engagement of CD21 in the B cell co-receptor complex by complement derived FDC-CD21L delivers an important co-signal. Coligation of BCR and CD21 facilitates association of the two receptors and the cytoplasmic tail of CD19 is phosphorylated by a tyrosine kinase associated with the B cell receptor complex (Carter et al. (1997) J. Immunol. 158, 3062-3069). This co-signal dramatically augments stimulation delivered by engagement of BCR by antigen and blockade of FDC-CD21L reduces the immune responses ~10- to ~1.000-fold.

BRIEF SUMMARY OF THE INVENTION

The present invention is directed to an artificial immune system to permit the assessment of allergens, immunogens, immunomodulators, immunotherapies, and potential vaccine agents without administration to animal subjects, comprising:
an engineered tissue construct; and
at least one three-dimensional artificial germinal center embedded in or fixed on the engineered tissue construct, said artificial germinal center comprising:
follicular dendritic cells;
B cells; and
T cells.

The artificial immune system of the present invention can be used in methods for evaluating the potential reaction of an animal to an agent. Such a method comprises administering an agent to the artificial immune system of the present invention and evaluating the B cell and/or T cell responses to said agent.

The artificial immune system of the present invention can also be used in methods for producing antibodies specific for an agent. Such a method comprises administering an agent to the artificial immune system of the present invention and isolating antibodies specific for said agent from the artificial immune system. In a similar manner, B cells producing antibodies specific for an agent, or T cells specific for an agent, can also be isolated from the artificial immune system of the present invention. The isolated B cells (which may be monoclonal for the agent in question) can be isolated, cloned and immortalized.

FDCs provide intact antigen to interaction with BCRs and this antigen-BCR interaction provides a positive signal for B cell activation and differentiation.

FDCs provide a complement derived CD21L for B cell-CD21 and this interaction with the CD21/CD19/TAPA-1 complex delivers a positive co-signal for B cell activation and differentiation.

FcγRIIB on FDCs bind Ig-Fc in the antigen-antibody complex and consequently the signal delivered via ITIM in the B cells may be blocked. (Note that FcγRIIB on the B cell is not engaged). Thus FDCs minimizes a negative signal to the B cell.

FDCs provide IC coated bodies (iccosomes), which B cells find highly palatable. Iccosomal antigen provides B cells with antigen to present to T cells.

Figure 2:
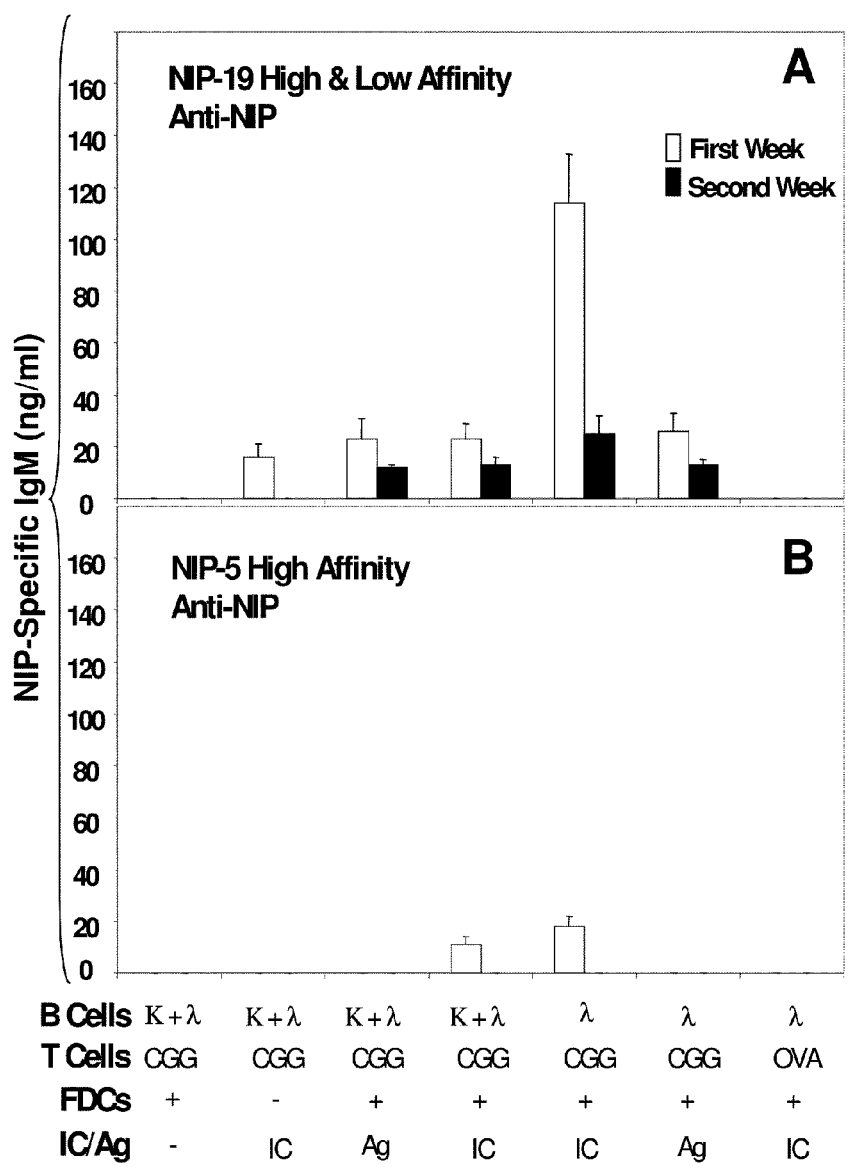

FIG. 2. FDCs promote the production of NP-specific IgM in cocultures with naïve B cells. Naïve $\lambda^+$ B cells and FDCs were isolated from naïve C57BL/6 mice and CCG-primed T cells were isolated from C57BL/6 mice immunized with CGG. ICs were prepared using NP-CGG and anti-CGG hyperimmune mouse serum. $\sim 1 \times 10^6$ naïve $\lambda^+$ B cells, $\sim 0.5 \times 10^6$ CGG primed T cells, $\sim 0.4 \times 10^6$ FDCs were cocultured in the presence or absence of 100 ng NP-CGG in ICs or as free antigen. Culture supernatant fluids were collected at day 7 and replaced with fresh media. NIP-specific IgM accumulated in supernatant fluids at day 7 and 14 of cell culture were measured using ELISA. All data are representative of three independent experiments. Panel A shows total NIP-specific IgM and Panel B shows high affinity NIP-specific IgM antibodies. White columns represent the NIP-specific IgM antibodies generated in the first week and the black columns represent the NIP-specific IgM generated in the second week. Affinity maturation of NIP-specific IgM was estimated by comparing the amount of NIP-specific IgM bound to $NIP_{19}$-OVA for total and to $NIP_5$-OVA for high affinity NIP-specific IgM antibodies. The error bars around the mean represent the standard error of the mean for replicate cultures.

Figure 1:
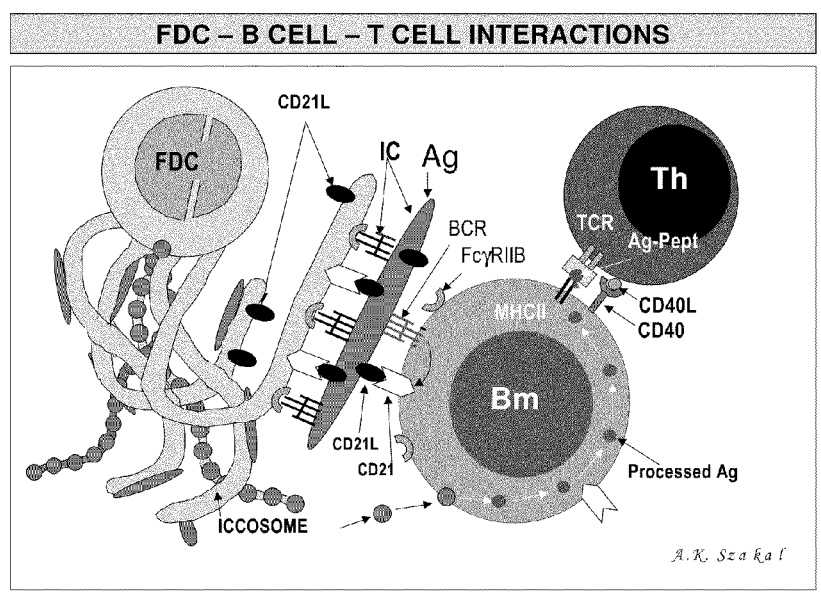
FIG. 1. Important receptors and ligands in signaling B cells. The need for B cell MHC II to present antigen to TCR is well known as is the involvement of CD40. Important events include.
Figure 3:
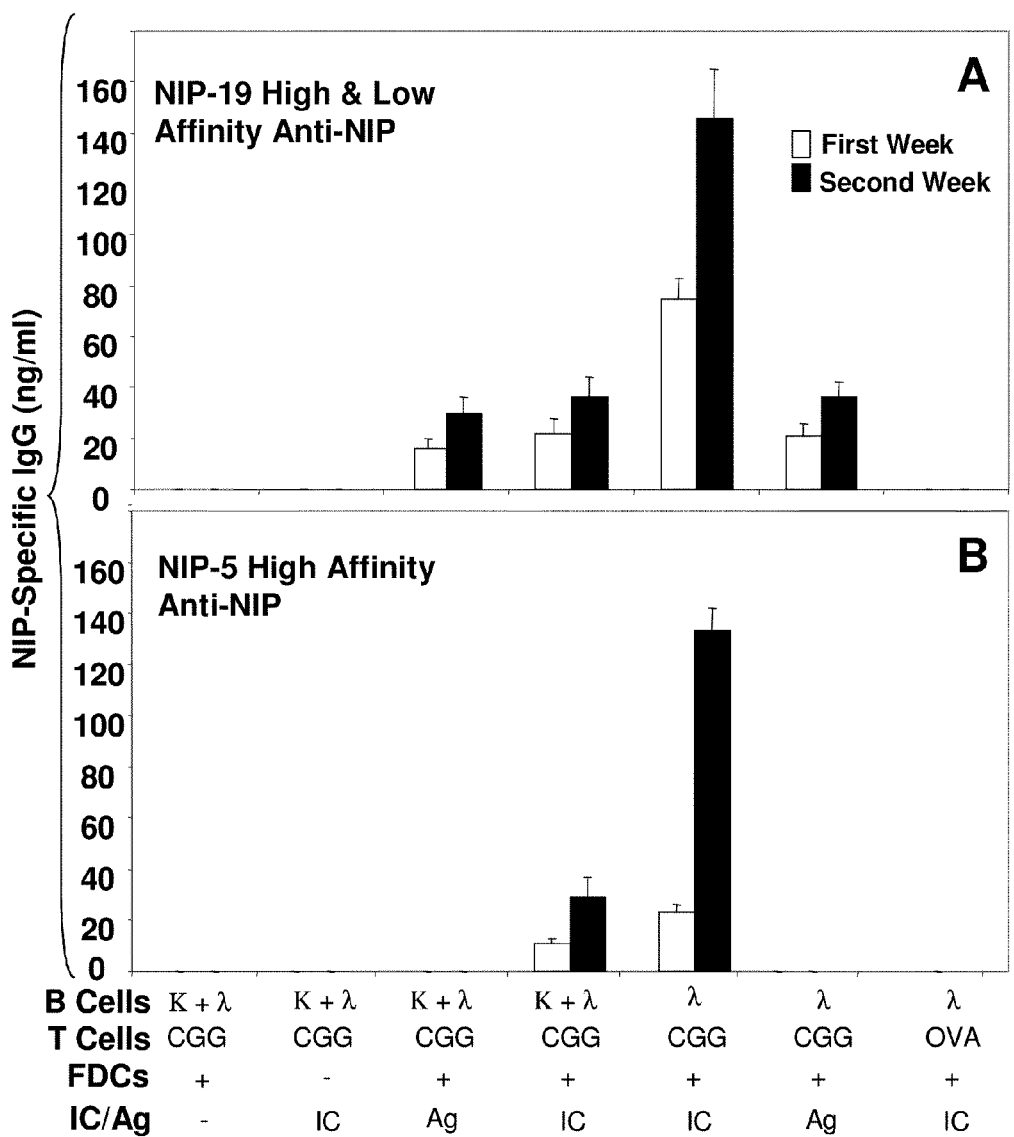

FIG. 3. FDCs promote production of NP-specific IgG and affinity maturation in cocultures with naïve B cells. The same cell cultures used to study production of NIP-specific IgM in FIG. 1 were used to study total and high affinity NIP-specific IgG antibodies. Culture supernatant fluids were collected at day 7 and replaced with fresh media. NIP-specific IgG accumulated in supernatant fluids at day 7 and 14 after cell culture were measured using ELISA. All data are representative of three independent experiments. Panel A shows total NIP-specific IgG and Panel B shows high affinity NIP-specific IgG antibodies. White columns represent the NIP-specific IgG antibodies generated in the first week and the black columns represent the NIP-specific IgG antibodies generated in the second week. Class switching from IgM to IgG was estimated by comparing the amount of IgM and IgG generated in the first vs the second week. Affinity maturation of NIP-specific IgG was estimated by comparing the amount of NIP-specific IgG bound to $NIP_{19}$-OVA and $NIP_5$-OVA. The difference between NIP-specific IgG bound to $NIP_{19}$-OVA and NIP-specific IgG bound to $NIP_5$-OVA reflects the affinity maturation of NIP-specific IgG antibodies. The error bars around the mean represent the standard error of the mean for replicate cultures.

Figure 4B:
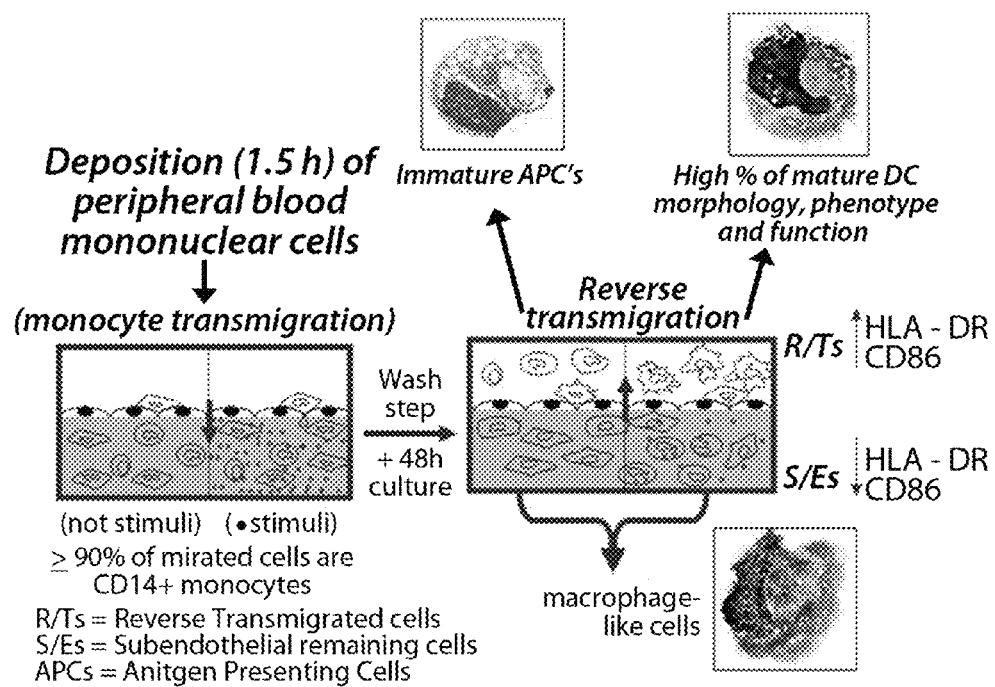
Figure 4C:
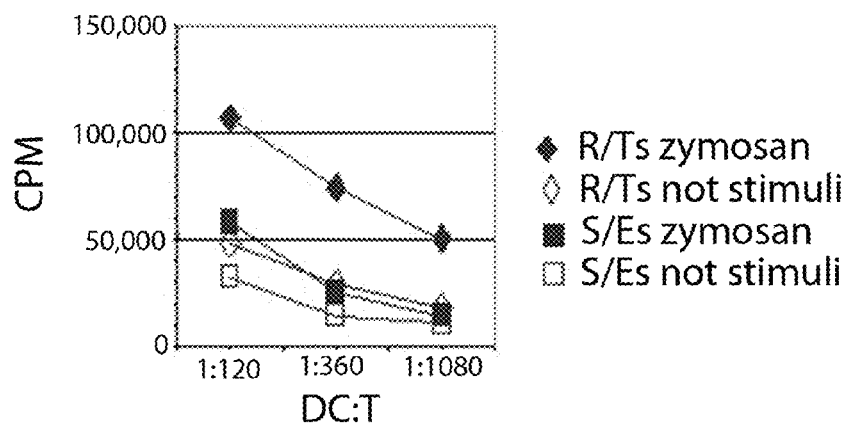

FIG. 4. Tissue setting model facts. From Randolph et al. (1998) Science 282, 480-3.

Figure 5:
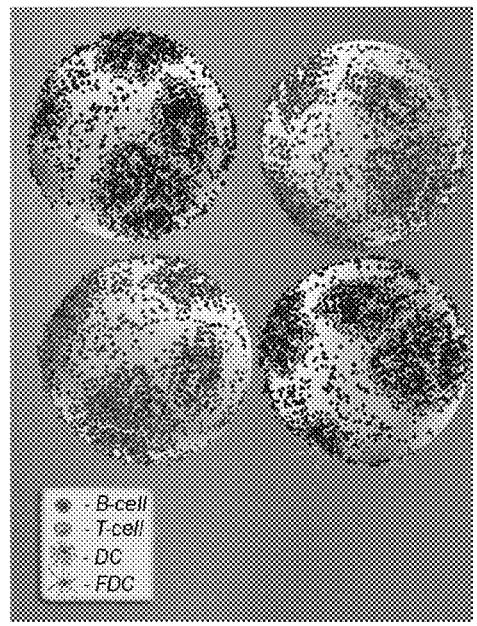

FIG. 5. A configuration of the in vitro LTE/GC that incorporates DCs, FDCs, T cells, and B cells on microcarriers.

Figure 6:
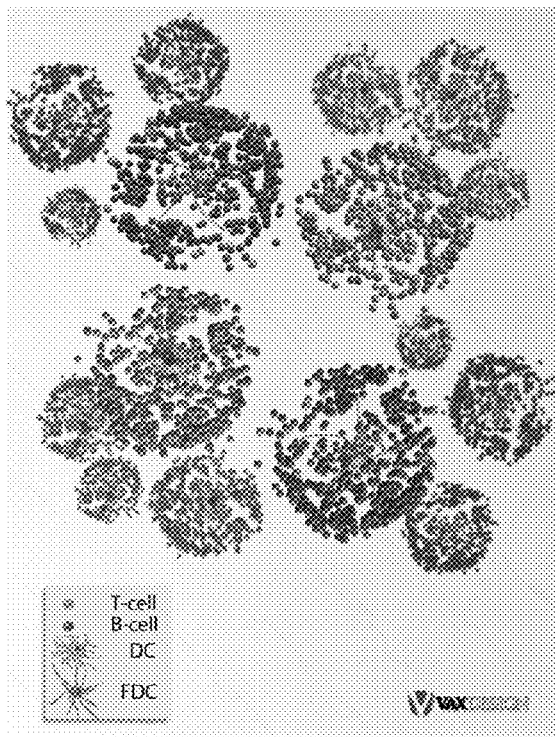

FIG. 6. Another configuration of the in vitro LTE/GC, which incorporates DCs, FDCs, T cells, and B cells in an ECM matrix.

Figure 7:
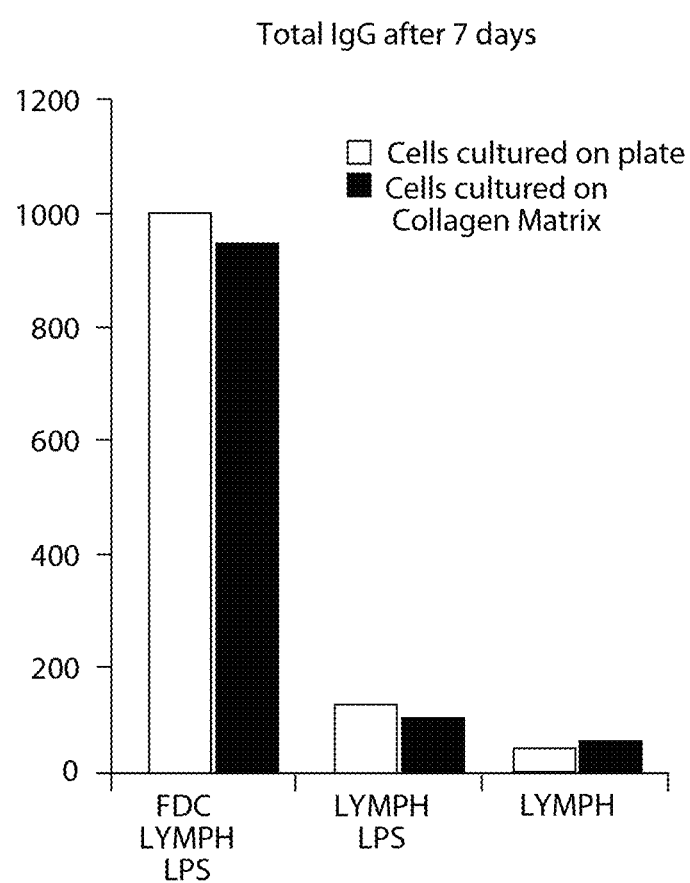

FIG. 7. IgG production after 7 days.

Figure 8:
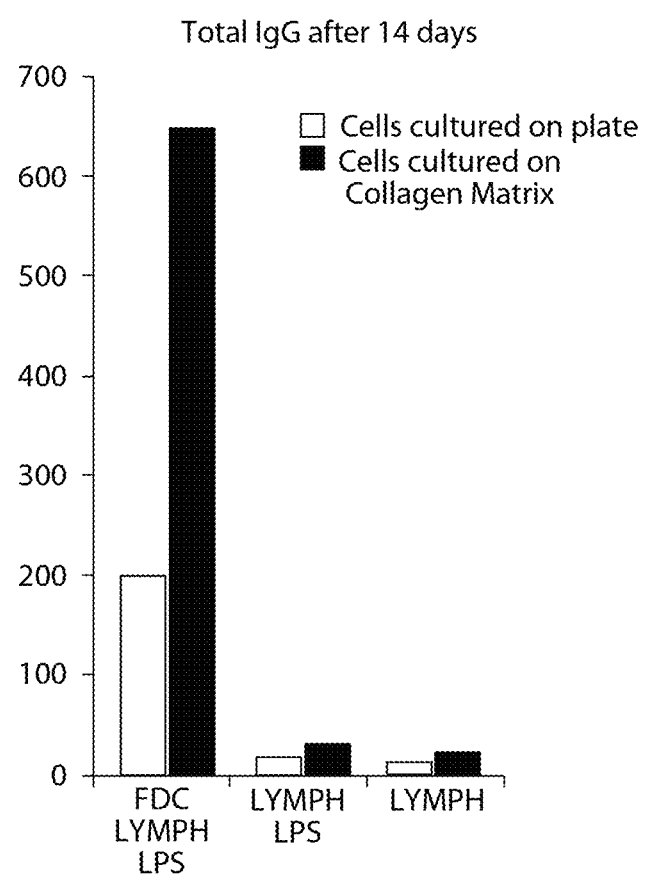

FIG. 8. IgG production after 14 days.

Figure 9:
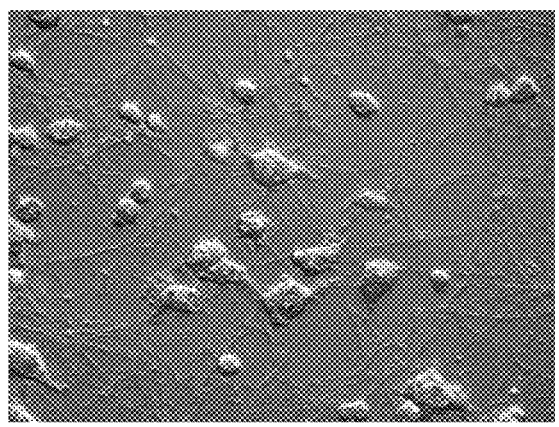

FIG. 9. Extensive processes are seen after the FDCs have been on collagen for about a week.

FIG. 10. To examine somatic hypermutation in the in vitro GCs, we used PCR to amplify the VH186.2 gene that is used in the mouse to make anti-NP. The PCR product was cut from an electrophoresis gel, extracted, and cloned; multiple clones were then sequenced. Of 20 readable sequences, 7 had homology to Vh186.2 germline and were designated VH186 clones. The sequences have been aligned against the VH186.2 germline-encoded gene. Mutations are indicated with the replaced nucleotide. Considerable mutation occurred in the variable gene, consistent with somatic hypermutation.

Figure 11:
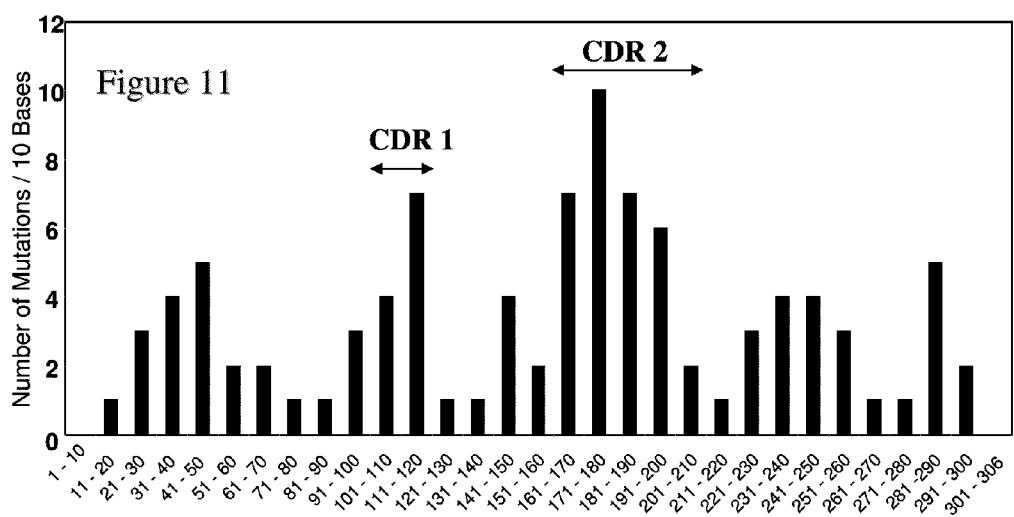

FIG. 11. The number of unique mutations per 10 nucleotide bases plotted against base position.

Figure 12:
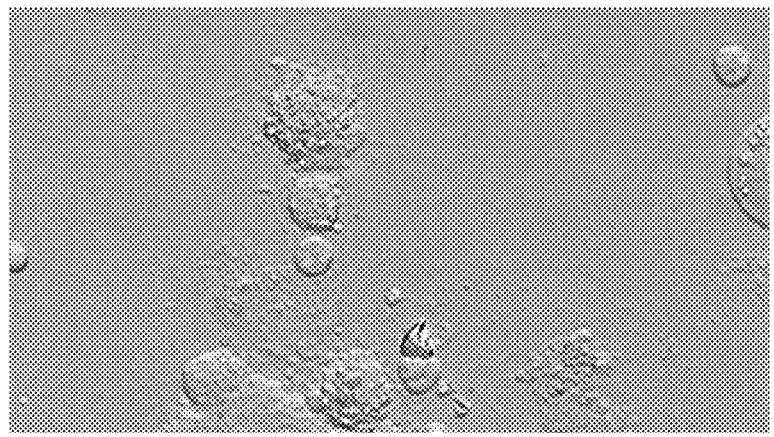

FIG. 12. FDCs after isolation but before positive selection.

Figure 13:
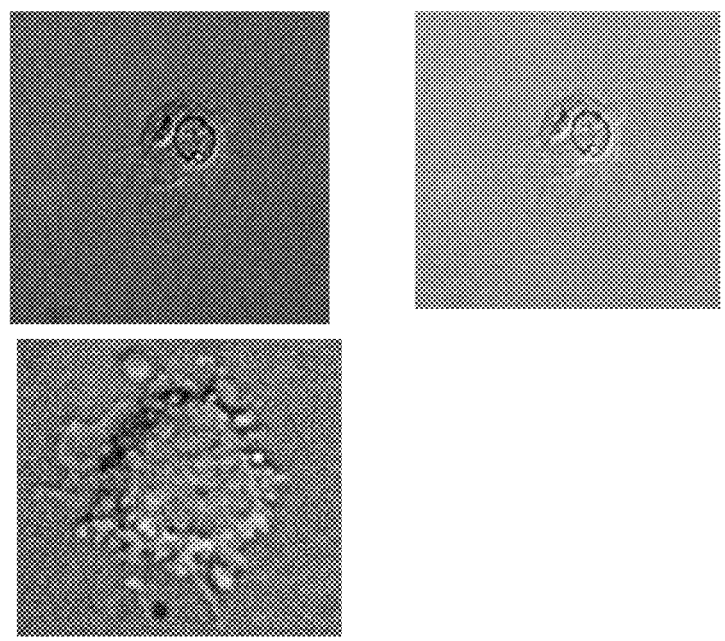

FIG. 13. Selected fresh FDCs after isolation but before positive selection. Note that some FDCs have processes.

Figure 14:
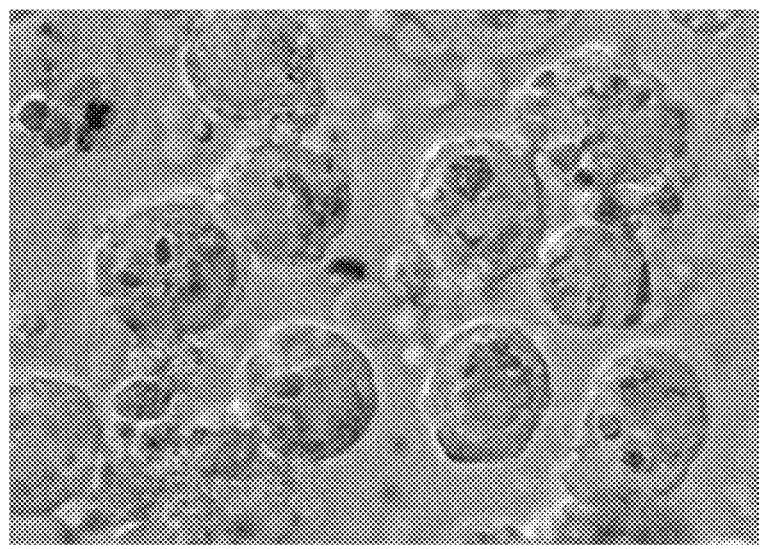

FIG. 14. FDCs after positive selection.

Figure 15:
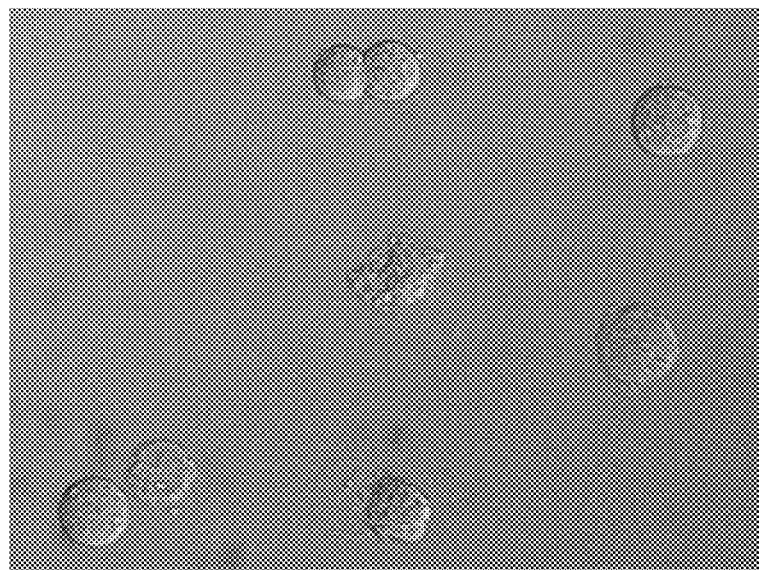

FIG. 15. FDCs after positive selection.

Figure 16:
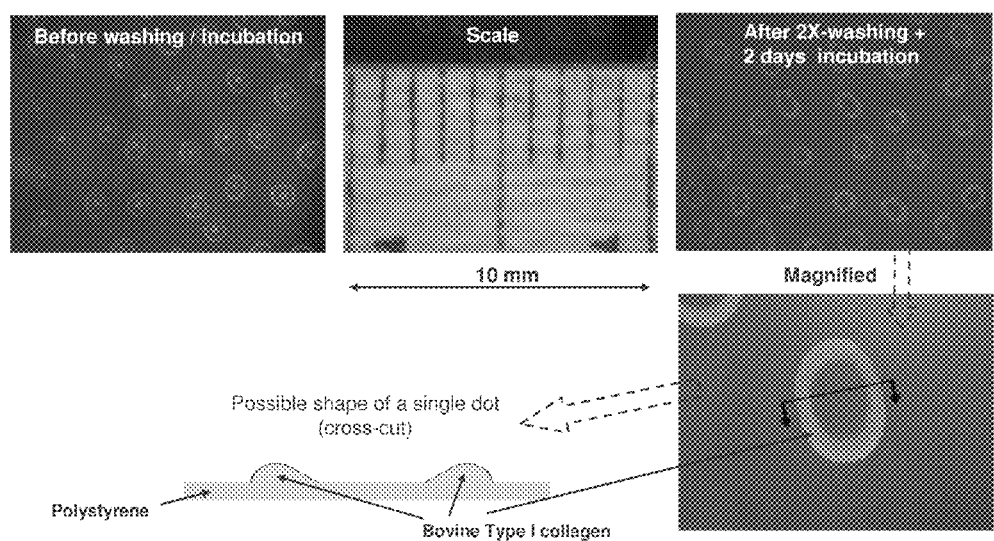

FIG. 16. Use of collagen dot pattern to create GC-like zones in vitro. Areas of preferred attachment of the FDC's are spatially limited to provide borders with "no FDC" zones.

Figure 17:
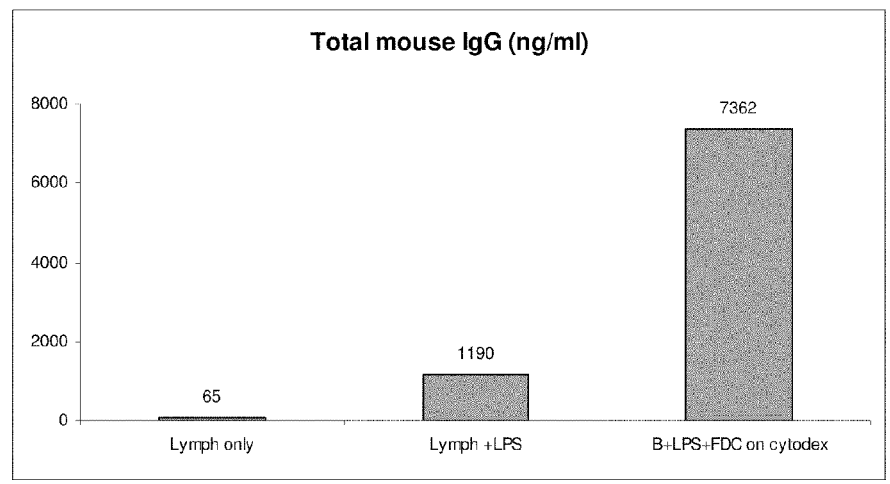

FIG. 17. FDCs were incubated on the Cytodex beads for 24 h and then the lymphocytes were added. 7 d later, IgG production was determined.

Figure 18:
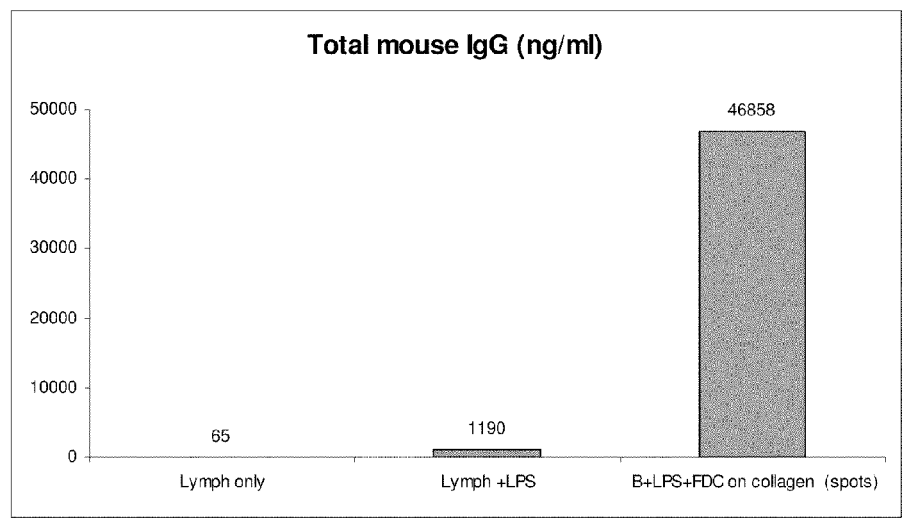

FIG. 18. FDCs were incubated on a collagen dot pattern plate for 24 h and then lymphocytes were added. 7 d later, IgG production was determined (this was on a non-tissue culture treated plate).

DESCRIPTION OF THE INVENTION

The present invention is an improvement on previously reported work, incorporating GCs into three-dimensional (3D) engineered tissue constructs (ETCs). In an embodiment of the present invention, we have incorporated the GC in the design of an artificial immune system (AIS) to examine immune (especially humoral) responses to vaccines, allergens, immunogens, immunomodulators, immunotherapies, and other agents. In an embodiment of the present invention, development of an in vitro GC adds functionality to an AIS, in that it enables generation of an in vitro human humoral response by human B lymphocytes that is accurate and reproducible without using human subjects. The invention also permits evaluation of, for example, vaccines, allergens, immunomodulators, immunogherapies and immunogens, and other agents, and activation of human B cells specific for a given antigen, which can then be used to generate antibodies. In an embodiment of the present invention the function of the in vitro GC is enhanced by placing FDCs and other immune cells in a 3D ETC; FDCs appear more effective over a longer time (antibody production is sustained for up to 14 days).

Embodiments of the present invention comprise placing FDCs in an ETC, such as a collagen cushion, gelatin, hyaluronic acid, small intestine submucosa, urinary bladder mucosa, PLGA, hydrogels, plates coated with collagen, microcarriers, inverted colloid crystal matricies, or other synthetic or natural extracellular matrix material, where they can develop in three dimensions. FDCs in the in vivo environment are attached to collagen fibers and do not circulate, as most immune system cells do. Thus, placing FDCs in, for example, a collagen matrix ought to be more in vivo-like. In other embodiments, in addition to creating the GC in 3D, a follicle with GC, T cell zones, and B cell zones in the scaffolding provided by the ETC matrix can be developed. Immobile FDCs form a center and the chemokines they secrete may help define the basic features of an active follicle.

Being able to reconstruct follicles where important events for productive humoral immune responses take place is of importance in assessing vaccines. For example, it is not uncommon to find non-responders to particular vaccine; such people may be put at risk when given a live vaccine. In an embodiment of the present invention, such non-responders can be identified by establishing a model of their immune system in vitro and determining their non-responsive or poorly responsive state before they were challenged with a live vaccine capable of causing harm. In another embodiment of the present invention, immunomodulators that could convert such poor responders into good responders can be identified and formulated for use in vivo. Such an approach has the potential to reduce vaccine development times and costs and to improve vaccine efficacy and reduce reliance on animal models.

The present invention can also be used for producing antibodies specific for an agent, B cells that produce antibodies specific for an agent, and/or T cells specific for an agent. In such embodiments, an agent (i.e. a vaccine, an adjuvant, an immunotherapy candidate, a cosmetic, a drug, a biologic, a proinflammatory agent, a chemical compound, an allergen, an immunogen, or an immunomodulator) is administered to the artificial immune system of the present invention. After enough time has passed for the artificial immune system to produce an immune response to the agent, antibodies specific for the agent, B cells that produce antibody specific for the agent, and/or T cells specific for the agent are isolated from the artificial immune system. The isolated B cells that produce antibodies (optionally monoclonal antibodies) specific for the agent and the isolated T cells specific for the antigen can be cloned and immortalized. Methods for immortalizing B cells and T cells are well known to one of skill in the art. See, for example, Aguirre et al., (2000) *J. Virol.* 74(2):735-743; and Robek et al. (1999) *J. Viol.* 73(6):4856-4865.

In addition, some therapeutic agents and industrial chemicals are toxic to the immune system and in other embodiments an in vitro immune system comprising in vitro germinal centers could be used to assess immunotoxicity and the effects of allergens in the context of a model human immune system. The present invention can also be used to assess therapeutic agents that could convert immune responders to non-responders, which would be invaluable for the treatment of antibody-mediated autoimmune disorders.

It has been observed that treatment of animals with LTβR-Ig disrupts FDCs' ability to retain immune complexes (ICs), which has been attributed to competition for B cell-derived LTα/β heterotrimers, thus reducing the ability to stimulate FDCs (Mackay & Browning (1998) *Nature* 395, 26-27). Under these conditions, FDCs appear to lose their activated phenotype and ICs tend to disappear. We have obtained similar results in vitro in and have shown that FDC function in promoting antibody production and blocking B cell apoptosis is adversely affected when the cells are incubated with LTβR-Ig.

Our data indicate that FDCs do not die as a consequence of lack of stimulation by LT or TNF and that they can exist for long periods in a resting state. Indeed, it has been reported that human FDCs survive in the absence of B cells for months in cell culture without proliferation although the antigenic phenotype (positive for DRC-1, CD21, CD23, CD35) disappears after only a few days (Tsunoda et al. (1990) *Virchows. Arch. B Cell. Pathol. Incl. Mol. Pathol.* 59, 95-105). Murine FDCs can also survive for months in culture and when present in an in vitro GC they maintain T cells, B cells, and a functioning immune system (Qin et al. (1999) *J. Immunol. Methods* 226, 19-27). We found that purified murine FDCs can survive for long periods (at least 6 weeks) in the absence of other cells. However, it appears that these resting FDCs can be activated by stimulation of the FDC with T cells and B cells, together with ICs and complement.

We have found that FDCs express CD40 and the level on freshly isolated FDCs appears to be higher than the level on B cells, suggesting that GC T cells may have an attractive receptor for their CD40L. Engagement of CD40 is known to activate B cells, dendritic cells, and macrophages. Given the importance of CD40 in activation of these immunologically relevant cells, FDC-CD40 may also be involved in FDC activation (Caux et al. (1994) *J. Exp. Med.* 180, 1263-1272). Some FDC markers (e.g., CD23) appear to be T cell-dependent and engagement of FDC-CD40 by CD40L on T cells in active GCs is likely important to full expression of the active FDC phenotype. Expression of the FDC-M2 antigen and CD21L are complement-dependent. The FDC-M2 antigen is now known to be a fragment of C4, which binds covalently to ICs on FDCs (Marie Kosco-Vilbois, personal communication). Similarly, a fragment of C3 binds covalently to ICs and forms the CD21L (Qin et al. (1998) *J. Immunol.* 161, 4549-4554). Thus, it appears that development, maturation, and full activation of FDCs requires B cells, T cells, and complement.

We have also examined FDC accessory molecules and accessory functions. FDCs, B cells, and T cells are clustered together in GCs and cell-cell contact appears to be important because we have yet to find an FDC accessory activity that will work well across a semi-permeable membrane (Wu et al. (1996) *J. Immunol.* 157, 3404-3411; Tew et al. (1997) *Immunol. Rev.* 156, 39-52). FDCs may produce important cytokines but clearly cell surface molecules are important in these cell-cell interactions. A review of some of our data was previously published (Tew et al. (2001) *Trends Immunol.* 22, 361-367).

Immunogens are quickly converted into immune complexes (ICs) by antibodies persisting in immune animals from prior immunization(s) and ICs form in primary responses as soon as the first antibody is produced. These ICs are trapped by FDCs and this leads to GC formation. Immune complexes are poorly immunogenic in vitro, yet minimal amounts of antigen (converted into ICs in vivo) provoke potent recall responses.

Our results indicate that FDCs render ICs highly immunogenic. In fact, in the presence of FDCs, ICs are more immunogenic than free antigen (Tew et al. (2001) *Trends Immunol.* 22, 361-367). A high density of FcγRIIB on FDCs bind Ig-Fc in the IC and consequently the ITIM (immunoreceptor tyrosine-based inhibitory motif) signal delivered via B cell-FcγRIIB may be blocked. Antigen-antibody complexes cross-linking BCRs initiate this inhibitory signal and FcγRIIB on B cells. BCR is not cross-linked with B cell FcγRIIB in the model and thus a high concentration of FcγRIIB on FDCs minimizes the negative signal to the B cell. In addition, FDCs provide IC-coated bodies (iccosomes), which B cells find highly palatable. The iccosome membrane is derived from FDC membranes that have antigen, CD21L, and Ig-Fc attached. Iccosomes bind tightly to B cells and are rapidly endocytosed (Szakal et al. (1988) *J. Immunol.* 140, 341-353). Binding of BCR and CD21 of the B cell to the iccosomal antigen-CD21L-Ig-Fc complex is likely important in the endocytosis process. The B cells process this FDC-derived antigen, present it, and thus obtain T cell help (Kosco et al. (1988) *J. Immunol.* 140, 354-360). Thus, these ligand-receptor interactions help stimulate B cells and provide assistance beyond that provided by T cells.

Another important molecule associated with FDC function is CD23. We found that serum IgE is suppressed in CD23 transgenic mice where high levels of CD23 are expressed on FDCs and B cells and some T cells (Payet-Jamroz et al. (2001) *J. Immunol.* 166, 4863-4869). When purified transgenic B lymphocytes were compared with controls in B cell proliferation and IgE synthesis assays in vitro, the two were indistinguishable. Similarly, studies of lymphokine production suggested that T cell function in the transgenic animals was normal. However, adoptive transfer studies indicated that IgE production was dramatically suppressed when normal lymphocytes were used to reconstitute transgenic mice, which would have high levels of CD23 on the radioresistant transgenic FDCs. Furthermore, when FDCs were isolated from the transgenic mice, FDC-dependent IgG production in cell culture was near normal but IgE production was dramatically reduced, suggesting that high levels of CD23 on FDCs can selectively suppress IgE responses (Payet-Jamroz et al. (2001) *J. Immunol.* 166, 4863-4869). Interestingly, IL-4 induces CD23 on B cells but does not appear to induce CD23 on FDCs. However, in mice immunized using complete Freund's adjuvant (CFA), the level of CD23 on the FDCs is dramatically increased (Maeda et al. (1991) In "Dendritic Cells in Lymphoid Tissues." Y. Imai, J. G. Tew & E. C. M. Hoefsmit, eds. Elsevier Science, Amsterdam, pp. 261-269). If CD23 is elevated, then unoccupied CD23 on FDCs may bind B cell surface-IgE and this could result in an inhibition of IgE production. Thus, FDCs bearing high levels of CD23 may selectively down regulate specific IgE responses and this may explain why IgE responses in CFA-immunized animals are relatively low. Furthermore, the association with CFA suggests CD23 on FDCs may be regulated by Th-1 lymphokines.

ICs trapped by FDCs lead to GC formation. GC formation is involved in the production of memory B cells, somatic hypermutation, selection of somatically mutated B cells with high affinity receptors, affinity maturation, and regulation of serum IgG with high affinity antibodies (Tew et al. (1990) *Immunol. Rev.* 117, 185-211; Berek & Ziegner (1993) *Immunol. Today* 14, 400-404; MacLennan & Gray (1986) *Immunol. Rev.* 91, 61-85; Kraal et al. (1982) *Nature* 298, 377-379; Liu et al. (1996) *Immunity* 4, 241-250; Tsiagbe et al. (1992) *Immunol. Rev.* 126, 113-141).

The GC is generally recognized as a center for production of memory B cells; we have found that cells of the plasmacytic series are also produced (Kosco et al. (1989) *Immunol.* 68, 312-318; DiLosa et al. (1991) *J. Immunol.* 1460, 4071-4077; Tew et al. (1992) *Immunol. Rev.* 126, 1-14). The number of antibody-forming cells (AFCs) in GCs peaks during an early phase (about 3 to about 5 days after secondary antigen challenge) and then declines. By about day 10 when GCs reach maximal size, there are very few AFCs present (Kosco et al. (1989) *Immunol.* 68, 312-318). During the early phase, GC B cells receive signals needed to become AFCs. The GC becomes edematous and the AFCs leave and we find them in the thoracic duct lymph and in the blood. These GC AFCs home to bone marrow where they mature and produce the vast majority of serum antibody (DiLosa et al. (1991) *J. Immunol.* 1460, 4071-4077; Tew et al. (1992) *Immunol. Rev.* 126, 1-14; Benner et al. (1981) *Clin. Exp. Immunol.* 46, 1-8). In the second phase, which peaks about 10-14 days after challenge, GCs enlarge, and the memory B cell pool is restored and expanded. Thus, production of B memory and fully functional and mature antibody responses appears to require GCs and FDCs.

Potentiating B cell viability can be done with or without FDCs present to enhance in vitro GC efficacy. A method is to add fibroblasts or other stromal cells, such as synovial tissue-derived stromal cell lines, the effects of which are to prolong B cell viability in vitro through cell-cell co-stimulation (e.g., Hayashida et al. (2000) *J. Immunol,* 164, 1110-1116). Another soluble agent that has been shown to increase naïve and memory B cell viability is reduced glutathione (GSH), perhaps through anti-oxidant activity (see Jeong et al. (2004) *Mol. Cells.* 17, 430-437). Although Jeong et al. did not see enhanced viability of GC B cells, they did significantly enhance naïve and memory B cells with fibroblasts and GSH, suggesting that peripheral B lymphocytes can be used to populate the in vitro GC. Other soluble factors, such as IL-4, CD40L and anti-CD40 have been shown to potentiate B cell viability (L. Mosquera's work and M. Grdisa (2003) *Leuk. Res.* 27, 951-956). Ancillary factors and cells that increase B cell viability with or without FDCs will enhance in vitro GC performance.

Compared with other leukocytes, FDCs have received little attention. An understanding of FDCs is important to an understanding of B lymphocyte maturation and antibody production. This lack of information on FDCs is likely because these cells are rare and fragile. Knowledge of more typical leukocytes has been derived largely from in vitro studies of isolated populations.

We have developed techniques to isolate and work with FDCs and FDC-lymphocyte interactions can now be studied in vitro along with antigen, antigen-antibody complexes, and polyclonal B cell activators. FDCs with appropriate ICs have remarkable accessory activity when interacting with B cells and can:

block apoptosis in B cells (Schwarz et al. (1999) *J. Immunol.* 163, 6442-6447; Qin et al. (1999) *J. Immunol. Methods* 226, 19-27),
  block ITIM (immunoreceptor tyrosine-based inhibitory motif) signaling in B cells stimulated by ICs (Aydar et al. (2004) *Eur. J. Immunol.* 34, 98-107),
  promote B cell proliferation stimulated by antigen or mitogen (Burton et al. (1993) *J. Immunol.* 150, 31-38).
  promote recall responses (Tew et al. (2001) *Trends Immunol.* 22, 361-367),
  induce virgin B cells to produce IgM and promote class switching to IgG (Kraal et al. (1982) Nature 298, 377-379; Liu et al. (1996) *Immunity* 4, 241-250; Aydar et al. (2005) *J. Immunol.* 174, 5358-5366), and
  promote somatic hypermutation and the development of high affinity antibodies (Aydar et al. (2005) *J. Immunol.* 174, 5358-5366).

These are important features of the humoral immune response.

In vivo FDCs exist in networks linked to collagen and collagen associated molecules. This linkage allows networks of FDCs to remain stationary while B cells and T cells move in and out of contact with the FDCs and associated antigen. This arrangement has been reconstructed in the in vitro GCs of the present invention.

We have established that FDCs have an ability to attach to collagen type I, collagen type IV, laminin, biglycan, fibronectin, and hyaluronic acid. Furthermore, we have established that FDCs attached to collagen reestablish a reticulum with interconnecting processes. This ability to attach to collagen and collagen associated molecules contrasts with their lack of ability to attach directly to plastic or glass. Our data indicate that antibody responses are improved when the FDCs are adhered to collagen and collagen-associated molecules.

Vaccination Site Model. Dendritic cells (DCs) are among the most potent antigen-presenting cells (APCs) and are the only known cell type with the capacity to stimulate naïve T cells in a primary immune response. Peripheral blood monocytes are widely accepted as a reliable source of precursor cells for DC generation in vitro. Such monocyte-derived DCs (mo-DCs) posses the overall phenotype and antigen-presenting abilities found in DCs in vivo.

A common generation technique for mo-DCs is based on using the cytokines GM-CSF and IL-4 for 5 days, leading to cells with an immature phenotype. After antigen priming for a subsequent 2 days, mo-DCs increase their co-stimulatory and antigen-presenting capabilities to a state called maturation.

Interestingly, Randolph et al. found that the likely naturally occurring process of monocyte transendothelial migration induces a process of differentiation into DCs in just 2 days, without addition of exogenous cytokines. This process starts with monocytes traversing a monolayer of endothelial cells in the luminal to abluminal direction, followed by a reverse transmigration to the luminal surface after a period of 48 hr of resting (interaction) within the extracellular matrix (susceptible of containing specific antigens).

In an embodiment of the present invention, the vaccination site model comprises a monolayer of endothelial cells (human umbilical vein endothelial cells, HUVECs) grown to confluency over a bovine type I collagen matrix (cushion). Other vaccination site models can also be employed, using various ECM materials instead of collagen. In embodiments of the present invention, the ECM can be in a cushion or a membrane configuration or an endothelium grown over a polycarbonate or other membrane (e.g., a Transwell). The whole monocyte differentiation process resembles what is believed to occur in vivo where naturally occurring diapedesis of monocytes into the tissues ends up with the development of tissue-resident macrophages and migratory dendritic cells escaping to the lumen of the lymphatics by traversing endothelial cells in the abluminal to luminal direction. In other embodiments, DC maturation can be achieved based on the presence of stimuli embedded in the matrix.

We have developed an in vitro system for the generation of immature DCs from migratory peripheral blood monocytes. In an embodiment of the invention, the system comprises a collagen membrane sealed on each side by a confluent monolayer of endothelial cells. The assembly of this in vitro vaccination site (VS) in an integrated bioreactor allows the generation of a bicameral device, with independent liquid flow. The upper chamber contains continuously circulating monocytes and the lower chamber receives the migratory immature DCs ready to be antigenically primed in situ. After a defined period, antigenically activated mo-DCs can be relocalized (e.g., by means of slow flow or chemokine attraction) to reside in a pre-established lymphoid tissue equivalent (LTE) for induction of specific immune responses. These mo-DCs will induce an immune response in the LTE that also contains the GC.

EXAMPLES

Unless otherwise indicated, all culture conditions were replicated (3-6 replicates depending on power calculations) and blocking antibodies were used over a range of concentrations (typically, ~1, ~10, ~100 µg/mL) and experiments were repeated to establish reproducibility. Typically, the dose of antigen in the antigen-antibody complexes is ~10 to ~50 ng/mL and these preformed antigen-antibody complexes are at slight antigen excess, where the stimulatory activity is optimal. The levels of antibody (anti-NIP, anti-TT, or total IgG) are measured using an ELISA (expressed as ng antibody/mL).

The frequency of B cells with a given antigen specificity can be determined with a modified ELISPOT assay, as described by Crotty et al. (2004) *J. Immunol. Meths.* 286, 111-122. Briefly, B cells isolated from the AIS will be stimulated for approximately 5 h with plate-bound antigen in an ELISPOT plate. Activated B cells that are specific for the particular antigen will secrete antibody, which will be captured on the plate-bound protein. Captured antibody can be detected in a colorimetric assay, and the number of spots provides a sensitive determination of the frequency of responding cells. A similar ELISPOT-based approach for secreted cytokines can also be used the estimate the number of antigen-specific T cells generated within an AIS. In another embodiment, intracellular labeling for cytokines produced following antigen-specific stimulation can provide a similar readout. For well-defined antigens, such as tetanus toxoid, the use of tetrameric complexes of MHC molecules with specific peptide can be used to determine the frequency of antigen-specific T cells by direct detection of the T cell receptor itself.

Direct analysis of activated B and T cells can also be performed by isolating the lymphocytes from the engineered tissue construct (ETC) matrix at different times following antigen encounter. Different ETC materials will require differing approaches to dissociate cells from a matrix. For example, collagenase can be used to disrupt a collagen scaffold.

A feature of B and T cell activation is that the cells rapidly proliferate following antigen encounter. To examine the strength of the lymphocyte response, B and T cell proliferation can be tracked by pre-labeling the cells with the fluorescent dye CFSE prior to their introduction into the lymphoid tissue equivalent (LTE), which can be thought of as an in vitro lymph node. CFSE is a stable, long-lived molecule that binds cytoplasmic proteins via an enzymatic reaction. This division-sensitive dye is equally distributed amongst daughter cells following cell division; thus, each divided cells will have half the CFSE fluorescence intensity of the parent cell. By flow cytometric analysis, up to about 8 to about 10 cell divisions can be detected within a population of proliferating cells.

Lymphocyte activation is also associated with changes in the expression of membrane proteins that regulate B and T cell function. A characteristic of naïve B cell activation is the switch in expression of surface IgM to other antibody classes (especially IgG). Additionally, upregulated expression of surface MHC and accessory molecules, such as CD54, CD58, CD80, and CD86, are suggestive of B cell activation, and increased expression of surface CD27 marks the acquisition of a memory phenotype in B cells. T cell activation is associated with altered expression of molecules that regulate their migration (CD11a, CD62L) and activation (CD28, CD25). Changes in the expression pattern of each of these surface molecules can be monitored using standard flow cytometry techniques and commercially available antibodies (e.g., those from BD Pharmingen, CA).

Production of soluble growth factors can be used to gauge the induction of antigen-specific lymphocyte responses. Secreted cytokines, including, but not limited to, IL-2, IFN-$\gamma$, TNF-$\alpha$, IL-4, IL-6, and IL-10, can be detected following antigen encounter. Expression of certain cytokine profiles, such as IL-4 and IL-10 that are expressed by only particular T cell subpopulations, can provide clues to the quality of the adaptive response being generated. Current, commercially available reagents allow for the detection of soluble cytokines at concentrations in the pg/mL range.

Generation of adaptive immune responses within the lymphoid tissue equivalent (LTE) of an AIS can be examined at about 7 to about 14 d following antigen administration, the time typically required for induction of measurable protective immunity during in vivo and in vitro responses. Changes in the expression pattern of soluble proteins that are indicative of B and T cell activation/differentiation can be examined in supernatants harvested from the LTE. Specifically, B cell activation triggers production of secreted antibody molecules that can be quantitated by ELISA using commercially available reagents (e.g., those from Bethyl Laboratories, TX). This sensitive technique can be used to detect class switching, an important trait of B cell maturation/differentiation, by examining the expression of different Ig classes (IgM, IgG, etc.). To determine antigen-specific antibody production, whole protein can be used to capture specific antibody in an ELISA. For example, in the well-established NP experimental model, NIP-5 and NIP-19 can be used to specifically detect the production of antibodies against NP with high and high/low affinities, respectively.

Example 1

Animals and Immunization. Normal 8 to 12 wk old C57BL/6 mice can be purchased from the National Cancer Institute (Frederick, Md.) or The Jackson Laboratory (Bar Harbor, Me.). The mice can be housed in standard plastic cages with filter tops and maintained under specific pathogen-free conditions. Food and water can be supplied ad libitum. CGG (chicken gamma globulin)-primed T cells were obtained after immunization with 20 µg CGG (Pel-Freez Biologicals, Rogers, Ark.) and ~5×10$^8$ heat-killed *Bordetella pertussis* precipitated in aluminum potassium sulfate (A7167, Sigma), as described previously (5,28). The mice were given a booster immunization 2 weeks later with ~50 µg CGG i.p. and by ~5 µg CGG s.c. injection into the front legs and hind footpads.

Example 2

Antibodies and Reagents. Mouse CD45R (B220) MicroBeads, mouse CD90 (Thy1.2) MicroBeads, anti-biotin MicroBeads, and MACS LS columns can be purchased from Miltenyi Biotec GmbH (Auburn, Calif.). Biotin-labeled rat anti-mouse $\kappa$ can be purchased from Zymed (San Francisco, Calif.). Alkaline phosphatase-labeled goat anti-mouse IgG (H+L), and alkaline phosphatase-labeled goat anti-mouse IgM can be obtained from, e.g., Kirkegaard & Perry Laboratories (Gaithersburg, Md.). Anti-mouse FDC (FDC-M1) and anti-mouse CD21/CD35 can be purchased from, e.g., Pharmingen (San Diego, Calif.). NIP$_{19}$-OVA (4-hydroxy-3-ioda-5-nitrophenylacetyl ovalbumin with 19 NIP groups/OVA), NIP$_5$-OVA (with 5 NIP groups/OVA), and NP$_{30}$-CGG can be obtained from, e.g., Biosearch Technologies (Novata, Calif.). Rat anti-mouse CD40 can be obtained from, e.g., Southern Biotechnology Associates, Inc. Low-tox-m rabbit complement can be purchased from, e.g., Cedarlane Laboratories Limited (Westbury, N.Y.); heat inactivation was accomplished by incubating the complement in a water bath at 56° C. for ~30 min. NP-CGG-anti-CGG ICs were prepared by incubating the antigen and antibody for 2 h at 37° C. at final ratio of 1 ng/ml NP-CGG to 6 ng/mL of mouse anti-CGG. The anti-CGG was obtained from hyperimmunized mice with anti-CGG IgG levels in excess of 1 mg/ml. In certain experiments complement-bearing ICs were made using low-tox-m rabbit complement at 1:12 dilution during the 2 h incubation. Anti-CD21/35 was converted into F(ab')$_2$ fragments using the Pierce (Rockford, Ill.) ImmunoPure F(ab')$_2$ preparation kit (Cat. # 44888). Anti-CD23 (clone B3B4) was provided by Dr. Daniel Conrad.

Example 3

FDC Isolation. FDCs were isolated from lymph nodes (axillary, lateral axillary, inguinal, popliteal, mesenteric, and paraaortic) of normal, young adult mice as described previously (5,28). Briefly, one day before FDC isolation the mice were exposed to whole body irradiation to eliminate most T and B cells (1000 rads, using a $^{137}$Cs source) (Kosco et al. (1992) J. Immunol. 148, 2331-2339). Lymph nodes were collected and each lymph node capsule was opened using two 26-gauge needles. The lymph nodes were then placed in an enzyme cocktail consisting of 1 ml collagenase D (16 mg/mL, C-1088882, Roche), 0.5 mL DNaseI (5000 units/mL, D-4527, Sigma), and 0.5 mL DMEM, supplemented with 20 mM HEPES, 2 mM glutamine, 50 µg/mL gentamicin, and MEM non-essential amino acids (GIBCO). After 30 min at 37° C. in a $CO_2$ incubator, the medium and released cells were removed and transferred to a 15 mL conical centrifuge tube containing 5 mL DMEM with 20% FCS and placed on ice. The remaining tissue was subjected to a second 30 min. digestion in a fresh aliquot of enzyme mixture and the cells were collected as before. Isolated cells were washed and then incubated with a rat anti-mouse FDC specific antibody (FDC-M1) for 45 min on ice. The cells were washed and incubated with 1 µg biotinylated anti-rat Ig specific for κ light chain for 45 min on ice. The cells were then incubated with 40 µL anti-biotin MicroBeads (Miltenyi Biotec) added to 360 µL MACS buffer for 15-20 min on ice. The cells were layered on a MACS LS column pre-wetted with 1 ml MACS buffer and washed with 10 ml of ice-cold MACS buffer. The LS column was removed from the VarioMACS and the bound cells were released with 10 mL MACS buffer. Approximately 85 to 95% of these cells express the FDC phenotype, FDC-M1$^+$, CD40$^+$, CR1&2$^+$, and FcγRII$^+$ (Sukumar et al., unpublished). Human FDCs can be isolated using positive selection with the FDC specific mAb HJ2, as previously described (Fakher et al. (2001) Eur. J. Immunol. 31, 176-185).

Example 4

Cell Cultures for Analysis of AID (activation-induced cytidine deaminase). Lymphocytes (~4×10$^6$) were co-cultured with ~1.6×10$^6$ FDCs in 48-well culture plates (CoStar; Cambridge, Mass.) for about ~2 d at 37° C. in a 5% $CO_2$ atmosphere. The wells contained ~1 mL/well of complete medium (DMEM, supplemented with 10% FCS, 20 mM Hepes, 2 mM glutamine, 50 µg/mL gentamicin, and MEM-nonessential amino acids). LPS at 10 ng/mL (L-2387, Sigma) or 100 ng/mL anti-CD40+10 ng/mL IL-4 (R&D Systems, Minneapolis, Minn.) were used to stimulate the lymphocytes. Suboptimal levels of LPS, anti-CD40+IL-4 were used because FDC co-stimulatory activity was most apparent at sub-optimal concentrations of the primary signal. The influence of FDCs was still apparent at higher concentrations of the primary signal but the differences were smaller and more difficult to study. After 48 h, cells were harvested and lysed using TRIzol (Invitrogen) and total RNA was extracted, following the manufacturer's protocol. In some experiments, λ$^+$ B cells and CGG-primed T cells and NP-CGG+anti-CGG immune complexes were cultured in the presence or absence of FDCs for 72 h. At the end of 72 h, B cells were isolated using anti-B220 MicroBeads and the MACS system. Total RNA from ~2×10$^6$ B cells was extracted using Trizol.

Example 5

Quantitative Reverse Transcriptase PCR analysis. The mRNA levels for AID (activation-induced cytidine deaminase) were measured using quantitative reverse transcriptase PCR (qRT PCR). The 18s rRNA level was used as an internal control to normalize the expression levels of AID. PCR reactions were performed in 96-well thin-wall PCR plates covered with transparent, optical-quality sealing tape (Bio-Rad). Amplifications were performed using the One Step RT-PCR kit (Applied Biosystems) under the following conditions: 48° C. for 30 min (cDNA synthesis), initial denaturation at 95° C. for 10 min, followed by 40 cycles of denaturation at 95° C. for 15 s and a combined annealing/extension step at 60° C. for 1 min. Data analysis was performed using the iCycler iQ software (BioRad). Finally, differences in mRNA expression levels were calculated using the $\Delta\Delta C_T$ method (Livak & Schmittgen (2001) Methods 25, 402-408). PCR efficiency was determined to be close to 100% by performing multiple standard curves using serial mRNA dilutions. An amplification cycle threshold value ($C_T$ value), defined as the PCR cycle number at which the fluorescence signal crosses an arbitrary threshold, was calculated for each reaction. The fold change between mRNA expression levels was determined as follows: Fold change=$2^{-\Delta\Delta C_T}$, where $\Delta\Delta C_T=(C_{T\ GoI}-C_{T\ Hk})$Sample−$(C_{T\ GoI}-C_{T\ Hk})$Control ($C_T$=cycle threshold, GoI=gene of interest, and Hk=house keeping gene).

Example 6

Purification of Naïve B Cells. Single cell suspensions were prepared by grinding lymph nodes from naïve mice between the frosted ends of two sterile slides in complete medium (DMEM supplemented with 10% FCS, 20 mM Hepes, 2 mM glutamine, 50 µg/mL gentamicin, and MEM-nonessential amino acids). The suspended cells were centrifuged (5 min., 1000 rpm, 4° C.) and resuspended in complete medium. The κ+λ-positive B cells (total B cells) were positively selected using anti-B220-bearing MicroBeads. Briefly, the lymphocytes were incubated with 40 µL anti-B220 MicroBeads (diluted 1:10 in MACS buffer) for 15-20 min on ice. The cells were layered on a MACS LS column pre-wetted with 1 ml MACS buffer and washed with 10 mL ice-cold MACS buffer. The LS column was removed from the VarioMACS and the bound cells were released with 10 mL MACS buffer, washed, and used as κ+λ-positive B cells. Anti-NP antibodies in C57BL/6 mice predominantly have λ light chains (Jack et al. (1977) Eur. J. Immunol. 7, 559-565; Reth et al. (1978) Eur. J. Immunol. 8, 393-400) and we reasoned that the NP response would be enhanced if λ-positive naïve B cells were enriched in culture. To obtain the λ-positive naïve B cells, we removed κ-positive B cells using 10 µg×light chain-specific biotinylated rat-anti-mouse mAb for 45 min on ice and trapped the κ-positive B cells on a MACS column with anti-biotin MicroBeads (Miltenyi Biotec). We reasoned that B220-positive cells in the flow through would express the λ chain and they were isolated using anti-B220, as described above. Naïve B cells express membrane IgM and the presence of IgM on our naïve B cell population was confirmed by flow cytometry. Single-cell suspensions of lymph node cells from normal mice were triple-labeled with FITC B220, PE-conjugated anti-mouse IgM, and biotin-labeled rat anti-mouse λ. The results indicated that about 95% of our B cells expressed κ rather than λ light chain. However, nearly 98% of the cells that expressed λ light chains were IgM-positive, which is expected of B cells in the naïve state. Serum anti-NIP levels in these donor mice were too low to measure (<1 ng/mL), again supporting the naïve nature of the NIP-specific B cells. The same approach can be used to obtain naïve human B cells from PBL; the markers will be IgM-positive and CD19-positive.

Example 7

Isolation of CGG-Primed T Cells. CGG-primed lymphocytes were obtained from draining lymph nodes of CGG-immunized mice a week or more after the CGG booster. Lymph nodes were surgically removed and ground between the frosted ends of two sterile slides. The cells were washed and incubated with 40 μL mouse anti-CD90 (Thy1.2) Micro-Beads (diluted 1:10 in MACS buffer) for ~45 min on ice then layered on a MACS LS column pre-wet with 1 ml MACS buffer and washed with ~10 mL ice-cold MACS buffer. The LS column was removed from the VarioMACS and the bound cells were collected as above. TT (tetanus toxoid)-primed T cells from seropositive humans can be obtained with anti-CD2.

Example 8

In vitro GC reactions and the Anti-NIP antibody Response. In vitro GC reactions were set up by co-culturing naïve λ positive B cells (~10×10$^5$ cells/mL), FDCs (~4×10$^5$ cells/mL), and CGG-primed T cells (~5×10$^5$ cells/mL), with NP-CGG+anti-CGG ICs (100 ng NP-CGG/well) in 48-well culture plates (CoStar; Cambridge, Mass.). The wells contained 1 mL/well complete medium (DMEM, supplemented with 10% FCS, 20 mM Hepes, 2 mM glutamine, 50 μg/mL gentamicin, and MEM-nonessential amino acids). ICs were prepared using NP-CGG and anti-CGG serum, and were used to stimulate the lymphocytes. The cultures were incubated at 37° C. in a 5% $CO_2$ atmosphere. Supernatant fluids were harvested on days 7 and 14 and were assayed for NIP-specific low and high affinity IgM and IgG antibodies, using a solid phase ELISA. Each experimental group was set up in triplicate.

Example 9

ELISA for Anti-NIP and Affinity. The relative affinities of anti-NIP antibodies were determined using an ELISA with OVA coupled to NIP at different ratios, respectively, $NIP_{19}$-OVA and $NIP_5$-OVA. NIP has higher affinity for anti-NP antibodies than NP and NIP was used for this reason (44,45). Briefly, flat-bottom 96-well ELISA plates (Falcon; Becton Dickinson, Calif.) were coated with 100 μg/mL $NIP_5$-OVA or $NIP_{19}$-OVA in PBS at 4° C. overnight. After washing the plates three times with 1×PBS containing 0.1% Tween 20, the plates were blocked with BSA (5%, 2 h, room temperature). Supernatant fluids from the cultures were then added to the plates at a starting dilution of 1:2 for wells with low responses and incubated at 4° C. overnight. Alkaline phosphatase-conjugated goat antibody specific for mouse IgM or IgG was added and incubated overnight. Alkaline phosphatase activity was visualized using a pNPP phosphatase substrate kit (Kirkegaard & Perry Laboratories, MD) and optical densities were determined at 450 nm. Standard curves for IgM or IgG were established by incubating the plates with 100 μg/mL affinity-purified goat anti-mouse IgM or IgG (Sigma, Saint Louis, Mo.). The plates were then washed and incubated with two-fold dilutions of mouse IgM or IgG (Sigma) starting at 100 ng/mL and the plates were incubated at 4° C. overnight. A standard curve was run on each plate and concentrations of anti-NIP IgM or IgG antibodies were calculated by comparison to standard curves in the linear dose range. The relative affinity of the antibodies was indicated by the level of antibody using $NIP_{19}$-OVA, which measures both high and low affinity anti-NIP versus $NIP_5$-OVA, which indicates only high affinity anti-NIP.

Example 10

Statistical Analysis. For analysis of ELISA readings, a t test (two-tailed distribution) was used. In some experiments, up to 5 different comparisons were made and a p value of less than 0.01 was required to account for multiple comparisons. The $2^{-\Delta\Delta C_T}$ method described in Livak & Schmittgen (2001) (*Methods* 25, 402-408) was used to analyze real-time quantitative PCR results.

Example 11

Histochemical procedures. A chapter, entitled "Use of monoclonal antibodies in immunocytochemistry at the light and electron microscopic levels" (Szakal et al. (1986). In Monoclonal Antibodies: Hybridoma Techniques. L. B. Schook, ed. Marcel Dekker, Inc, New York, pp. 229-263) describes these in detail. Biotinylated probes allow the use of HRP avidin and allow both light- and electron micrococopic-level studies.

Example 12

Studies on in vitro GCs. Promotion of NIP-specific IgM responses in in vitro GCs. Stimulation of antigen-specific B cells and class switching takes place in GCs; FDCs may enhance IgM responses and Ig class switching. To assess this, we isolated naïve, IgM-expressing B cells where a switch from producing IgM to IgG could be easily monitored. NIP-specific antibody responses were initiated in the in vitro GCs using λ light chain-expressing B cells (λ B cells) from normal mice, carrier-primed T cells (CGG-T cells) from CGG immune mice, FDCs from normal mice, and ICs consisting of NP-CGG-anti-CGG. After overnight incubation, FDC-lymphocyte clusters were seen, resembling those described by Kosco et al (1992) (*J. Immunol.* 148, 2331-2339); these clusters persisted through the 14 days of culture. It seems that naïve B cells initially produced IgM; as indicated in FIG. 2A (4$^{th}$ open bar), over 120 ng of IgM anti-NIP accumulated by day 7, using this combination of immunogen and cells.

Anti-NIP is largely derived from λ-bearing B cells and the use of purified λ B cells was helpful as naïve B cells containing κ and λ B cells (κ+λ B cells) in normal amounts (~95% κ) did produce IgM anti-NIP (~20 ng/mL), but not as well as the λ-bearing cells (FIG. 2, open bars 3 vs. 4). Use of ICs that could be trapped and presented to B cells by FDCs was also important, as free antigen (NP-CGG) did not work as well as ICs (FIG. 2, open bar 4 versus 5). If either immunogen (antigen or ICs) or FDCs were missing or if OVA-primed T cells were substituted for CGG-primed T cells, the NIP-specific IgM response was typically undetectable. The low IgM response obtained with ICs in the absence of FDCs at day 7 in this experiment was not a consistent observation. The culture media were replaced on day 7 and some IgM accumulated in the second week (FIG. 2, solid bars), but the levels were low compared with anti-NIP IgM in the first week. The assay using NIP-5 to detect high affinity antibody indicated very little IgM anti-NIP was produced, even in the presence of FDCs (FIG. 2, panel B).

Example 13

Immunoglobulin class switching and NIP-specific IgG Responses in in vitro GCs. The IgG anti-NIP-response was studied in the same cultures described in FIG. 2 for the NIP-specific IgM. The need for λ B cells, CGG-primed T cells, FDCs, and NP-CGG-anti-CGG ICs was the same for optimal IgG production and was apparent, as it was for IgM (FIG. 3A; $3^{rd}$ open and $3^{rd}$ filled bars). The anti-NIP IgG that accumulated in the first week in FIG. 3A was about half the level of anti-NIP IgM in FIG. 2A (~60 ng/mL IgG versus ~120 ng/mL IgM). However, these relationships were reversed in the second week with over ~140 ng/mL IgG versus only ~20 ng/mL of IgM (filled bars in FIG. 2A versus 3A). Thus, the Ig isotype produced switched from predominantly IgM in the first week to predominantly IgG in the second week.

Example 14

In vitro affinity maturation detection and importance of FDC-ICs. In contrast to IgM, large amounts of IgG were apparent when NIP-5 was used to detect high affinity antibodies. Of interest, only about 30 to 50% of the IgG made in the first week was of high affinity (NIP-5 versus NIP-19). However, almost all of the IgG made in the second week was of high affinity (FIG. 3B). This is consistent with selection of high affinity B cells and selective stimulation of these cells to produce the high affinity IgG associated with affinity maturation. Furthermore, affinity maturation was only observed when antigen was in the form of ICs that would be trapped and presented to B cells by FDCs. Free antigen (NP-CGG) that should engage BCR efficiently did stimulate low affinity IgG (FIG. 3A, $1^{st}$ and $4^{th}$ filled bars) but did not stimulate detectible levels of high affinity IgG (FIG. 3B). In the absence of FDCs, ICs engage BCR and FcγRII leading to ITIM activation, SHIP phosphorylation, and a lack of responsiveness. Trapping the Ig-FC by high levels of FcgRII on FDCs minimizes engagement of FcgRII on the B cell and facilitates a productive IgG response (Aydar et al. (2004) *Eur. J. Immunol.* 34, 98-107; Aydar et al. (2003) *J. Immunol.* 171, 5975-5987). Thus, it appears that the only ICs capable of stimulating B cells for a productive IgG response are those trapped by the FDCs.

Example 15

Gauging the importance of FDC CD21-CD21 ligand interactions to IgM responses and class switching. Interaction between FDC-CD21 ligand and CD21 in the B cell co-receptor complex (CD21/CD19/CD81) is important for FDC-associated antigen to stimulate optimal recall responses (Tew et al. (2001) *Trends Immunol.* 22, 361-36; Qin et al. (1998) *J. Immunol.* 161, 4549-4554). IgM responses in CD21/CD19 knockout mice are also depressed (Chen et al. (2000) *Immunol. Rev.* 176, 194-204). Thus, blocking signals to B cells delivered via FDC-CD21 ligand-CD21 interactions may inhibit IgM production and class switching. Our results indicate that anti-CD21 inhibited the IgM response and, consistent with a reduction in class switching, the IgG response was dramatically reduced (>90%) at its peak in the second week. The diminished IgG response was not simply attributable to a loss of B cells in the absence of CD21 ligand-CD21 interactions because the number of B cells persisting in cultures treated with anti-CD21 was not significantly lower than the B cell number with the isotype control. We also considered the possibility that the Fc portion of the intact IgG binding B cell-CD21 could engage B cell-FcγRII and lead to ITIM activation and thus explain the reduced antibody response with anti-CD21. However, if the anti-CD21 is simply blocking the receptor then anti-CD21 F(ab')$_2$ should work as well as the intact antibody and this proved to be the case.

Both FDCs and B cells express CD21 and CD23. CD23 is a ligand for CD21 in the human system (Aubry et al. (1992) *Nature* 358:505), raising the possibilities that anti-CD21 could influence FDC activity or that FDC-CD23 could engage B cell CD21 and provide a signal to B cells. However, treating FDCs with anti-CD21 did not inhibit their activity and treating B cells and FDCs with anti-CD23 did not have any detectible effect.

We sought to determine whether increasing CD21 ligand levels on FDCs would increase class switching and production of high affinity NIP-specific IgG. Treating ICs with complement to enhance CD21 ligand levels on the FDCs did not increase the anti-NIP response. This is consistent with previous data where additional CD21 ligand did not increase the murine anti-OVA response in normal mice (Aydar et al. (2002) *Eur. J. Immunol.* 32, 2817-2826). However, in aged mice the level of CD21 ligand covalently bound to the FDCs appears to be low and addition of rabbit complement to increase levels of FDC-CD21 ligand on aged FDCs improved accessory activity and the B cell responses (Aydar et al. (2002) *Eur. J. Immunol.* 32, 2817-2826).

Example 16

AID expression and the presence of FDCs. AID is important in class switching and is expressed in GC-B cells and in B cells undergoing class switch recombination in vitro (Muramatsu et al. (1999) *J. Biol. Chem.* 274, 18470-18476; Muramatsu et al. (2000) *Cell* 102, 553-563; Faili et al. (2002) *Nat. Immunol.* 3, 815-821). FDCs may help regulate AID expression by GC-B cells; we sought to examine this. Expression of AID mRNA can be detected in lymphocytes stimulated with LPS, or with IL-4+ anti-CD40, where a large proportion of B cells are stimulated with these polyclonal B cell activators. Costimulation of B cells with FDCs might amplify AID mRNA. Quantitative RT-PCR was used to determine the levels of AID mRNA. Suboptimal amounts of LPS (10 ng), IL-4 (10 ng), and anti-CD40 (100 ng) were used to stimulate low levels of AID in the lymphocytes. FDCs were added either at the beginning to provide costimulation or at the end of the culture so that mRNA coming from the FDCs would be constant in all cultures. AID mRNA level in normal lymphocytes was defined as 1-fold to compare the effect of LPS, or IL-4+ anti-CD40 treatment alone or in the presence of FDCs. Analysis with RT-PCR indicated that LPS increased AID in the lymphocyte population about 8-fold and FDCs about 2-fold. However, the combination of FDCs with LPS was synergistic and AID mRNA expression increased about 130-fold. Results with IL-4+ anti-CD40 were similar. The combination of FDCs with IL-4+ anti-CD40 resulted in AID mRNA levels up ~180-fold versus ~3-fold with FDCs and about 18-fold with IL-4+ anti-CD40.

No significant AID mRNA was found when FDCs alone were stimulated with LPS or anti-CD40+IL-4 suggesting that B cells were the source of the mRNA when FDCs and B cells were cultured together. This was confirmed by isolating mRNA from B cells purified after the two-day culture period using B220 MicroBeads with the MACS system. Nearly all of the AID mRNA was in the B cell fraction; while the flow-through fraction did contain detectable activity, it also contained some contaminating B cells, likely accounting for this AID mRNA. Furthermore, the increased AID activity in B cells did not appear to be simply attributable to increased B cell survival or proliferation caused by FDCs, because the same number of B cells (~2×10$^6$) was used to obtain the mRNA and the 18s rRNA was used as an internal loading control. Thus, the level of AID mRNA per B cell was elevated when B cells were cultured in the presence of FDCs.

Example 17

CD21-CD21 ligand interactions involvement in AID expression and class switching. The reduction in class switching observed when CD21 ligand-CD21 interactions were blocked suggests that the interaction between FDC-CD21 ligand and B cell-CD21 might signal through the co-receptor complex and help regulate expression of AID. To examine this, anti-CD21/35 was used to interrupt FDC-CD21 ligand-B cell-CD21 interactions and the level of AID expression was reduced ~90%, indicating that this interaction is playing a role.

Example 18

Importance of ICs and CD21 ligand for FDC-mediated enhancement of AID responses. We sought to determine whether ICs contribute to the ability of FDCs to promote optimal high affinity antibody responses. Given the importance of FDC-ICs in promoting class switching and affinity maturation, we sought to determine whether ICs and CD21 ligand-CD21 interactions were important in FDC-mediated enhancement of AID expression in the NP-CGG system. The small number of B cells responding to NP-CGG makes the study of AID regulation more challenging. However, it was possible to detect FDC-mediated enhancement of AID mRNA when ~2×10$^6$ purified B cells were used for RNA purification after 72 h of culture. NP-CGG-anti-CGG ICs stimulated enhancement, while NP-CGG failed to stimulate detectible enhancement. Furthermore, anti-CD21/35 inhibited the antigen-stimulated response in the same fashion as was observed in studies of B cells stimulated with polyclonal activators.

Example 19

Somatic hypermutation in the in vitro GCs. To examine somatic hypermutation in the in vitro GCs, we used PCR to amplify the VH186.2 gene that is used in the mouse to make anti-NP. The PCR product was cut from an electrophoresis gel, extracted, and cloned; multiple clones were then sequenced. 7 out of 20 readable sequences had homology to Vh186.2 germline and were designated VH186 clones. The sequences have been aligned against the VH186.2 germline-encoded gene. Mutations are indicated with the replaced nucleotide. As illustrated in FIG. 10, considerable mutation occurred in the variable gene, consistent with somatic hypermutation. These mutations were more frequent in the CDR sequences (FIG. 11). Analysis of the mutations revealed:
- an average of 41 mutations (range 32-45) were seen per VH186 gene (306 nucleotides) sequenced. This is high, consistent with results obtained in studies of in vivo GCs.
- most mutations were point mutations with one deletion. This is also typical of in vivo germinal centers and somatic hypermutation.
- all mutations except one were replacement mutations in the CDRs while the ratio of replacement to silent mutations in the framework regions was almost 1:1, both indicating strong selective pressure.
- a predominance of transitions over transversions was observed.
- we observed only one mutation in all the Cγ regions sequenced, providing an internal control for the fidelity of PCR amplification.

The mutational characteristics obtained in these in vitro GCs are similar to those observed in GCs in vivo for anti-NP responses. Thus, the in vitro GCs of the present invention appear to faithfully reflect important events that occur in GCs in vivo.

Example 20

CXCL 13, a chemokine secreted by FDCs has been shown to attract human B cells and T cells into the follicular zones (Estes et al. (2004) *J. Immunol.* 173, 6169-6178). In other embodiments, blocking this chemokine or its receptor CXCR 5 may inhibit migration of B and T cells to the FDC-rich areas. Additionally, GC B cells are activated and express a unique phenotype, PNA$^+$, GL-7$^+$, CD95$^{hi}$ and CD23$^{lo}$ and segregate into light zones where they are centrocytes and into dark zones where they are centroblasts. In other embodiments, these features can be present in the in vitro model of the lymph node follicle.

Example 21

In other embodiments, purified preparations of FDCs, B cells, or T cells can be embedded into ETCs, including, e.g., cellulose-based microcarriers, collagen cushions, and lymph node extracellular materials. This can be done by adding cells to the ETC suspensions before they solidify or by directly injecting a suspension into the ETCs. These cells can be allowed to equilibrate in the matrix and can then be visualized and followed over a period of 2 weeks. Human B and T cells can be isolated from peripheral blood of healthy donors by negative selection using anti-14, -CD19, -CD3, and -CD56, to remove unwanted cells. Murine B and T cells can be obtained from lymph nodes and purified by positive selection, as previously described.

Example 22

As FDCs can co-stimulate B cells without MHC or species restriction, in embodiments of the present invention, FDCs can be isolated from either lymph nodes of naïve mice or human tonsils surgically removed from young patients, using the FDC-specific mAb HJ2, as previously described (Fakher et al. (2001) *Eur. J. Immunol.* 31, 176-185).

Example 23

In other embodiments, different procedures such as "in situ jellification", "injection", "cushion-beads combinations", plus combinations with small cushions, a single cushion for all cell types, and perforations in the cushions, can be used for the general LTE architecture when incorporating FDCs. In other embodiments, the ETC can include, e.g., collagen cushions, cellulose based microcarriers, synthetic and other natural bio-materials, and/or lymph node extracellular materials.

Example 24

In further embodiments, FDCs, T cells, and B cells can be placed in the same ETC but at different locations. The FDCs can be put in first and allowed to attach to ETC and then the T and B cells can be placed near by. Lymphocytes will be attracted to the FDCs, where they can cluster around the FDCs and form in vitro GCs. We have observed that the CD3-selected T cells and negative-selected B cells exhibit low cell motilities in collagen cushions in the absence of chemokines. The presence of FDCs and associated chemokines may increase the natural motility of lymphocytes.

Example 25

In still other embodiments, FDCs, T cells, and B cells can be placed in single ETCs to visualize clustering or in separate ETCs to simulate T and B cell areas of a lymph node. In addition to regular microscopic analysis, cells can be fluorescently labeled in the cushion and visualized by confocal microscopy. Furthermore, in other embodiments, B and T lymphocytes isolated from tetanus toxoid (TT)-immunized persons can be co-cultured in these FDC-containing ETCs and further stimulated with TT-anti TT ICs, to serve as models for antigen-specific GCs.

Example 26

FDCs secrete the chemokine CXCL 13, which acts as a chemoattractant for both B cells and follicular T helper cells, recruiting these cells into the GC (54). In other embodiments, B and T cells can be added to the FDC-containing ETCs and stimulated using, e.g., LPS or Con A in the presence or absence of neutralizing antibodies against CXCL13 or its receptor, CXCR5. In other embodiments, FDCs from CXCL13 knockout mice can be used. In other embodiments, anti-CD21, anti-ICAM-1, anti-VCAM, and anti-BAFF antibodies can be separately added to these cultures to examine the importance of these surface molecules in the formation of FDC-B cell-T cell clusters. Previous studies have indicated a role for these molecules in the clustering of B cells around FDCs in culture wells.

Example 27

Characteristics of GCs and inclusive B cells when FDCs are loaded with antigen. GCs are formed about 6 to 8 days after primary antigen challenge and are detected by the presence of FDCs decorated with ICs and complement fragments in the light zones present next to dark zones consisting of rapidly dividing B cells expressing the unique GC B cell phenotype (PNA$^+$, GL-7$^+$, CD95$^{hi}$, CD23$^{lo}$. These GC B cells are B cells responding to the specific antigen and undergo class switching and somatic hypermutation, generating IgG antibodies of higher affinity.

Example 28

In other embodiments, B and T cells isolated from TT-immunized individuals can be cultured in collagen cushions containing FDCs and stimulated with TT-anti TT ICs. After about 10 days in culture, B cells can be harvested and labeled and analyzed for surface expression of PNA, GL-7, CD95 and CD23 by flow cytometry. Detailed analysis of the morphology of these follicles can also be made using confocal microscopy.

Example 29

In still other embodiments, B and T cells isolated from antigen-immunized individuals can be cultured in collagen cushions containing FDCs and stimulated with antigen-anti antigen ICs. After about 10 days in culture, B cells can be harvested and labeled and analyzed for surface expression of PNA, GL-7, CD95 and CD23 by flow cytometry. Detailed analysis of the morphology of these follicles can also be made using confocal microscopy.

Example 30

In the 2D clusters we have studied in vitro, we have not seen B cells forming a mantle area around the GC or T cells, collecting together to form a separate unit. However, the 2D arrangement has no reticular fibers or other structures to help arrange the cells. In other embodiments of the present invention, ETCs can be used to provide conditions such that T cells and B cells segregate around the GC and form distinct areas. The cells surrounding the GCs can be examined using T cell- and B cell-specific antibodies. Labeling with anti-IgD may also be informative because GC B cells do not express IgD, whereas mantle zone B cells do.

When secondary lymphoid tissues are challenged with appropriate antigens they expand dramatically, as a consequence of large numbers of new follicles developing with active GCs. These follicles are organized with distinct T cell zones and B cell zones and an active GC consists of rapidly proliferating B cells, helper T cells, FDCs, and macrophages cleaning up apoptotic B cells that have not received survival signals from FDCs. Each active GC is further divided into a light zone where FDCs, T cells, and B cells are interacting and a dark zone where the B cells are rapidly proliferating.

Follicles are apparent not only in lymph nodes but in spleens, lymphoid nodules (e.g., Peyer's patches) and are conserved in all species with lymph nodes. It does not appear to matter whether the antigen is brought into the follicle from the afferent lymph, as it is in a lymph node, or from the blood via the marginal sinus of the spleen or by M cells (as is the case in Peyer's patches).

Once antigen is in the follicle, the agonist necessary for development of a secondary follicle with an active GC and development of humoral immunity is present. The follicular structure, fully developed in 3D, is likely important to the production of adequate amounts of high affinity antibody.

Example 31

When lymphoid tissues are digested and the cells are placed into conventional tissue culture they lose the follicular organization and remain disorganized in 2D. In embodiments of the present invention, FDCs can be added to such cultures to form FDC-B cell-T cell clusters. We have demonstrated immunoglobulin class switching, somatic hypermutation, and affinity maturation in such in vitro GCs.

Example 32

In embodiments of the present invention, follicular leukocytes can be placed in an ETC matrix, natural or synthetic, where FDCs can be fixed and T and B cells can arrange themselves around the FDCs to recreate aspects of the in vivo environment of the follicle. Suitable materials for the ETC include collagen, gelatin, hyaluronic acid, extracellular matrix (ECM), small intestine submucosa, urinary bladder mucosa, PLGA, hydrogels, inverted colloid crystal matrices, microcarriers, and plates coated with collagen. In other embodiments of the present invention, there is no ETC matrix; the T cells, B cells, and FDCs are simply cultured in standard, 2D wells.

Example 33

In other embodiments of the present invention, a functional LTE containing FDCs and established or non-established T and B cell zones can be used to assess vaccines. The FDCs can be used to assist in establishing the T and B cell zones; they do not need to be pre-formed. Likewise, in another embodiment, the T and B cell zones are not required. In primary immune responses, monocyte-derived dendritic cells primed from the integrated in vitro vaccination site can be used, Model antigens, such as tetanus for a recall response and influenza to validate the model in a primary response, can be used, as can other antigens, immunogens, and/or allergens.

Example 34

In studies using murine cells, we present evidence for a functional in vitro GC in 2D culture. Specifically, murine GCs were set up in vitro by co-culturing naïve λ-positive B cells, FDCs, NP-CGG (chicken gammaglobulin)+anti-CGG ICs, and CGG-primed T cells. This resulted in FDC-lymphocyte clusters and production of anti-NIP IgM and IgG.

Class switching was indicated by a shift from IgM in the first week to IgG in the second week and affinity maturation was indicated by a change from mostly low affinity IgM and IgG in the first week to virtually all high affinity IgG anti-NIP in the second week. Class switching and affinity maturation were easily detectable in the presence of FDCs bearing appropriate immune complexes (ICs) but not in the absence of FDCs or FDCs with irrelevant antigens in ICs.

Free antigen plus FDCs resulted in low affinity IgG, but affinity maturation was only apparent when FDCs bore ICs. Class switching is activation-induced cytidine deaminase (AID)-dependent and blocking FDC-CD21 ligand-B cell CD21 interactions inhibited FDC-IC-mediated enhancement of AID production and the IgG response. FDCs promoted the production of both AID and error-prone polymerases; these enzymes are needed for somatic hypermutations. Sequencing of the variable region genes indicated large number of mutations consistent with the production of high affinity antibodies.

Example 35

In an embodiment of the present invention, a human cell system in a 3D engineered tissue construct is constructed that can be integrated in an AIS. The FDCs can attach to collagen fibers, which provide a scaffold in which GCs can develop in 3D, as they would in vivo. NIP-specific IgM and IgG production, class switching, somatic hypermutation and affinity maturation established in the murine system can be compared with the results from previous studies using the 2D in vitro GCs.

Example 36

In an embodiment of the present invention, human GCs can be established using tetanus toxoid (TT) as a carrier, because TT-specific memory T cells are abundant in most people. In other embodiments, NP-tetanus toxoid can be used to set up the GCs. Anti-NP production can then be examined as this allows simple determination of the production of both high and low affinity antibodies and allows examination of affinity maturation. In other embodiments naïve human T cells can be primed in vitro and then used to provide T cell help for the in vitro GCs. Naïve human T cells can be primed with CGG, using monocyte-derived DCs from either culture or from in vitro vaccination site (VS) cells pulsed with CGG. Such primed T cells can then be used in the same way as used for the murine system with CGG-NP.

Example 37

FDCs are attached to reticular fibers in vivo and are in immobile networks in the follicles. The lymphocytes recirculate but the FDCs are stationary. However, the FDCs in this condition in vivo have matured. Collagen cushions made from rat-tail collagen were established. FDCs attached and set up clusters on the collagen.

Example 38

The inclusion of immune complexes in the in vitro LTE is important for the generation of fully differentiated memory B cells. In an embodiment of the present invention, a two-stage LTE is used. In the first step, naïve antigen-specific B cells are stimulated to produce antibody in a T cell-dependent manner. Immune complexes and memory T cells elicited from this construct, in concert with FDC, provide the signals to trigger a fresh batch of naïve B cells to fully differentiate in the second LTE construct.

In another approach, ICs can by generated by artificially coupling antibody to antigen in a non-specific manner. For example, a hapten is conjugated to the antigen of interest, which is then be bound by a specific antibody. Fluorescein isothiocyanate (FITC) can be linked to primary amino groups of target protein using literature procedures, with special attention taken to retain the antigenicity of the protein after conjugate formation. In this regard, Fluorescein-EX or other derivatives bearing elongated linkers may be advantageous over tight linker-antigen conjugates formed by FITC and other haptens. Commercially available high-affinity anti-FITC antibodies can then be used to bind the antigen-hapten conjugate, forming a complete IC. Tetanus toxoid can be used as a model antigen because most adults have immunized been with it and humoral and cell-mediated immune responses generated against this antigen are well characterized. Other linkers and antigens, such as digoxin and NP, respectively, can also be used. In another embodiment, the antibody can be chemically coupled directly to the antigen using the amine-thiol cross-linking method. Using these non-specific chemistries does not require an agglutination step, making them useful for polyclonal antibodies. Additionally, the stoichiometry of the IC can be manipulated without affecting the size or density of this complex.

Example 39

In this example, an experiment was conducted, adding LPS to B cells to provide a signal and then adding FDCs to provide a costimulatory signal. Antibody production was then examined. We followed the cells for 2 weeks. Culture media were collected at the end of the first week and the titers represent antibody synthesis from days 1 to 7. The media were replaced and the supernatant fluids were collected at day 14; those titers represent antibody synthesis from days 7 to 14. FDCs had potent costimulatory activity, as expected but at 7 days there was no difference in antibody production between FDCs attached to collagen and FDCs floating on the plastic plate. However, at day 14 the FDCs attached to the collagen were about three times as active in promoting antibody production when compared with those floating on the plastic plates. The IgG response in the second week was lower than the first week but this is typical for LPS-stimulated cells, which respond rapidly and taper off rapidly. In contrast, antigen-stimulated cells typically reach a peak in IgG production in the second week. These results demonstrate that putting FDCs on collagen enhances biological activity.

Example 40

FIG. 12 illustrates freshly isolated FDCs. A few FDCs can be found with typical processes before positive selection using the monoclonal antibody, FDC-M1. However, after positive selection, few processes persist (FIGS. 13, 14, 15).

Example 41

We sought to induce primary human IgG responses in vitro and to generate high quality antibodies with an affinity that will enable them to function at low concentrations. Ovalbumin (OVA) was used as an example antigen; the blook donor used was OVA-seronegative. T cells were primed with monocyte derived DCs. Monocytes (~1×10$^7$) were cultured with IL-4 (~1000 U/mL) and GM-CSF (~800 U/mL) to generate immature DCs. After 5 d, OVA (1 μg/mL) was added to provide antigen for processing and LPS (1 μg/mL) was added to stimulate DC maturation. After 8 h, ~20×10$^6$ CD4$^+$ T cells were added for OVA priming. The priming and maturation for helper T cells was allowed to continue for 5 d in the mouse experiment (experiment 1) and 10 d (experiment 2). After this priming period, the T cells and DCs were mixed with naïve B cells (~15×10$^6$) in experiment 1 and ~10×10$^6$ in experiment # 2. OVA (~5 μg)+murine anti-OVA (~30 μg) were complexed to generate OVA ICs and the cells and ICs were injected behind the neck of irradiated mice for experiment # 1 and the ICs were placed in vitro with ~3×10$^6$ freshly isolated FDCs for experiment # 2. Thus, in experiment 1 we obtained ~30 ng/mL of anti-OVA at day 14.

In experiment 2, at day 5, we measured specific anti-OVA at ~12 ng/mL. At day 10 the anti-OVA levels were at ~20 ng/mL. (these levels were readily assessed by ELISA). Thus, in 50 mL of media, this corresponds to ~600 ng of anti-OVA at day 5 and ~1000 ng of total anti-OVA for day 10. We next tested for affinity maturation. The test was to let the anti-OVA bind to the ELISA plate and then to add a high salt concentration and quantitate how much of the bound antibody dissociates over 2 h on a shaker. The plates were then washed and the ELISA was conducted as before. Low affinity antibody will dissociate and be washed away and high affinity antibody will remain bound and detected in the ELISA. Most of the day 5 antibody dissociated with 1 M NaCl and most of the day 10 antibody remained bound, implying that over that time period there was a change from low to high affinity antibodies.

Example 42

Total mouse IgG produced by fresh murine FDCs on collagen type I beads after incubation with murine lymphocytes and LPS and with or without IC and complement. In this example, we sought to activate the FDCs by adding fresh immune complexes and complement after they had set up networks on collagen. We measured ~8-9000 ng of antibody with fresh FDCs, After 7 days, FDCs with ICs, the antibody concentration was still ~8-9,000 ng/mL. After 14 d, the antibody concentration was 4-5000 ng/mL with ICs and FDCs maintained on the beads being better than those maintained on plastic. Thus, the FDCs may be maintained with good activity on beads for at least about 2 wk. Human FDCs benefited from ICs and complement.

Example 43

Direct deposition of collagen without chemical crosslinking. In this example, PuraCol (ultra-pure bovine Type I collagen in 1 mM nitric acid, Inamed, Calif.) solution (~50 μL) was placed in a 250 μL plastic pipette tip and used as a 'pen' for manual patterning, without a pipette. This method allowed the printing of oval and circular spots (~800-1000 μm) that were able to endure washing and incubation with a cell culture. The tissue culture plates or Petri dishes thus spotted with collagen were placed in a biohazard hood and dried for ~1 h under the UV light of the hood. The tissue culture (multi-well) plates or Petri dishes patterned with collagen as described were filled with PBS and incubated at room temperature for ~10 min. The dishes were then emptied, filled with distilled water and incubated for ~5 min. This distilled water wash was repeated three times, after which the dishes were dried in the biohazard hood for 3 h, including ~30 min further exposure to the UV light (FIG. 16).

Example 44

Deposition of collagen with chemical crosslinking. In another embodiment, to increase hardiness of the collagen spots, methods of chemical crosslinking can be used. As an example, glutaraldehyde can be added to the washing/neutralizing solution to initiate crosslinking of the collagen. Unreacted glutaraldehyde can be neutralized by washing with solution of trimethylamine, and removed via multiple washes with distilled water.

Example 45

Patterning by laser micromachining. In another embodiment, continuous coating of the dishes with collagen and subsequent patterning using laser beam is a method that can be used to create regular patterns. Laser micromachining can also be useful in the chemical modification and activation of the plastic surfaces that would improve attachment and stability of the collagen patterns.

Example 46

Memory B cells are formed in large numbers in germinal centers in vivo. They are also found in the in vitro germinal centers of the present invention. To assess this, we took human lymphocytes 12 d after the start of the in vitro primary and added fresh FDCs and immune complexes to provoke a secondary response. Supernatant fluids from these cultures were collected and contained measurable levels of high affinity specific IgG antibody.

Example 47

In an embodiment of the present invention, one can induce primary responses against dangerous immunogens in vitro and expand the specific memory cells in an in vitro GC and then use these memory cells with more FDCs and immunogen to further expand the cultures. This process can be repeated one or more times. The final product is large amounts of high-affinity, specific human IgG antibodies without exposing a human to the dangerous immunogen.

Example 48

FIG. 16 illustrates collagen dots prepared according to Example 43. The results in FIG. 17 are with collagen-coated Cytodex beads and the ~7,000 ng of IgG/mL with FDCs on Cytodex is a typical result. The results in FIG. 18 are with the collagen dot pattern. There, we measured ~47,000 ng of IgG.

An embodiment of the present invention comprises having FDCs adhered to the collagen dots, where they attract lymphocytes. The collagen dots can be prepared with, for example, bovine collagen or rat tail type 1 collagen (FIG. 16). The collagen can also be used to cover the base of tissue culture plate wells, for example. A high level of antibody resulted (~29,500 ng/mL).

Without wishing to be bound by any mechanism, it seems that some FDCs stick to the top of the collagen dots, while others form a ring around the bottom of the dots. Those sticking to the top form irregular shaped clusters and appear to attract lymphocytes; the lymphocytes become more dispersed further away from the FDC network.

While the foregoing specification teaches the principles of the present invention, with examples provided for the purpose of illustration, it will be appreciated by one skilled in the art from reading this disclosure that various changes in form and detail can be made without departing from the true scope of the invention.

What is claimed is:

1. An in vitro method for assessing the potential of a subject to immunologically respond to a vaccine, comprising:
   a) administering a vaccine to an in vitro cellular system, wherein the in vitro cellular system comprises a culture comprising an engineered tissue construct, and at least one three-dimensional artificial germinal center embedded in or fixed on the engineered tissue construct, wherein the artificial germinal center comprises a plurality of follicular dendritic cells (FDCs), a plurality of B cells, and a plurality of T cells, and where the B cells and T cells are cells isolated from the same subject; and
   b) evaluating B cell, T cell, or both B cell and T cell responses to said vaccine, wherein a poor B cell or T cell response or no B cell or T cell response identifies the subject as having a low potential of immunologically responding to the vaccine.

2. A method of evaluating a test agent for adjuvant activity, comprising,
   a) repeating step a) of claim 1, wherein a test agent is administered in conjunction with the vaccine to the in vitro cellular system;
   b) evaluating B cell, T cell, or both B cell and T cell responses to said vaccine; and
   c) comparing the responses with those found in step b) of claim 1 where the test agent was not administered to the in vitro cellular system.

3. The method of claim 1, wherein said engineered tissue construct is selected from the group consisting of a collagen cushion, gelatin, hyaluronic acid, small intestine submucosa, urinary bladder mucosa, PLGA, a hydrogel, and a tissue culture plate coated with collagen, microcarriers, inverted colloid crystal matrices, synthetic extracellular matrix materials, or natural extracellular matrix materials.

4. The method of claim 2, wherein said engineered tissue construct is selected from the group consisting of a collagen cushion, gelatin, hyaluronic acid, small intestine submucosa, urinary bladder mucosa, PLGA, a hydrogel, and a tissue culture plate coated with collagen, microcarriers, inverted colloid crystal matrices, synthetic extracellular matrix materials, or natural extracellular matrix materials.

5. The method of claim 1, wherein said culture further comprises follicular leukocytes.

6. The method of claim 2, wherein said culture further comprises follicular leukocytes.

7. The method of claim 1, wherein said engineered tissue construct comprises a tissue culture plate coated with collagen spots.

8. The method of claim 2, wherein said engineered tissue construct comprises a tissue culture plate coated with collagen spots.

9. The method of claim 7, wherein said collagen spots are crosslinked.

10. The method of claim 8, wherein said collagen spots are crosslinked.

11. The method of claim 7, wherein said follicular dendritic cells are adhered to the collagen spots.

12. The method of claim 8, wherein said follicular dendritic cells are adhered to the collagen spots.

13. The method of claim 1, wherein said in vitro cellular system further comprises stromal cells distributed in the engineered tissue construct.

14. The method of claim 2, wherein said in vitro cellular system further comprises stromal cells distributed in the engineered tissue construct.

15. The method of claim 1, wherein said culture further comprises soluble factors selected from the group consisting of IL-4, CD40L, and anti-CD40 antibodies.

16. The method of claim 2, wherein said culture further comprises soluble factors selected from the group consisting of IL-4, CD40L, and anti-CD40 antibodies.

17. The method of claim 1, wherein a T cell response to the vaccine is evaluated.

18. The method of claim 2, wherein a T cell response to the vaccine is evaluated.

19. The method of claim 1, wherein a B cell response to the vaccine is evaluated.

20. The method of claim 2, wherein a B cell response to the vaccine is evaluated.

21. The method of claim 1, wherein the FDCs are obtained from the same subject as the T cells and B cells.

* * * * *

SEQUENCE LISTING

<160> NUMBER OF SEQ ID NOS: 1

<210> SEQ ID NO 1
<211> LENGTH: 240
<212> TYPE: DNA
<213> ORGANISM: Mus musculus

<400> SEQUENCE: 1

```
ggtgtccact cccaggtcca actgcagcag cctggggctg agcttgtgaa gcctggggct      60
tcagtgaagc tgtcctgcaa ggcttctggc tacaccttca ccagctactg gatgcactgg     120
gtgaagcaga ggcctggacg aggccttgag tggattggaa ggattgatcc taatagtggt     180
ggtactaagt acaatgagaa gttcaagagc aaggccacac tgactgtaga caaaccctcc     240
```